US012332974B2

(12) United States Patent
Kim et al.

(10) Patent No.: US 12,332,974 B2
(45) Date of Patent: Jun. 17, 2025

(54) DETERMINATION OF DATA-SOURCE INFLUENCE ON DATA MANIFESTATIONS

(71) Applicant: Ancestry.com DNA, LLC, Lehi, UT (US)

(72) Inventors: Andre Everson Kim, Upland, CA (US); Alisa Elnaz Sedghifar, San Francisco, CA (US); Ross Eugene Curtis, Cedar Hills, UT (US); Caitlyn Elizabeth Bruns, Saratoga Springs, UT (US)

(73) Assignee: Ancestry.com DNA, LLC, Lehi, UT (US)

( * ) Notice: Subject to any disclaimer, the term of this patent is extended or adjusted under 35 U.S.C. 154(b) by 0 days.

(21) Appl. No.: 18/759,587

(22) Filed: Jun. 28, 2024

(65) Prior Publication Data

US 2025/0005108 A1  Jan. 2, 2025

Related U.S. Application Data

(60) Provisional application No. 63/511,084, filed on Jun. 29, 2023.

(51) Int. Cl.
*G06F 16/00* (2019.01)
*G06F 18/2415* (2023.01)

(52) U.S. Cl.
CPC .............................. *G06F 18/2415* (2023.01)

(58) Field of Classification Search
None
See application file for complete search history.

(56) References Cited

U.S. PATENT DOCUMENTS 4,201,386 A  5/1980 Seale et al.
5,115,504 A  5/1992 Belove et al.
(Continued)

FOREIGN PATENT DOCUMENTS

CN       109121436 A  *  1/2019  ......... G06F 16/2246
WO   WO 2008/042232 A2     4/2008
(Continued)

OTHER PUBLICATIONS

Alexander, D.H. et al., "Enhancements to the ADMIXTURE Algorithm for Individual Ancestry Estimation," BMC Bioinformatics 12(1), 246, Jun. 18, 2011, pp. 1-6.
(Continued)

*Primary Examiner* — Tuankhanh D Phan
(74) *Attorney, Agent, or Firm* — Fenwick & West LLP

(57) ABSTRACT

Disclosed are methods and system for predicting data-source influences on one or more data manifestations of a named entity. The method includes receiving an inheritance dataset of the named entity. The method determines first and second portions of the inheritance dataset of the named entity. The method determines an aggregated data-bit association score for the named entity based on the inheritance dataset at an identified subset of the data-bit regions. The method determines aggregated data-bit association scores associated with the first and second data source based on the first and second portions of the inheritance dataset at the identified subset of the data-bit regions. The method selects one of the first and second data sources as having a measure of influence on a data manifestation of the named entity corresponding to the identified subset of the data-bit regions.

20 Claims, 12 Drawing Sheets

(56) References Cited

U.S. PATENT DOCUMENTS

| | | | |
|---|---|---|---|
| 5,246,374 | A | 9/1993 | Boodram |
| 5,413,908 | A | 5/1995 | Jeffreys |
| 5,467,471 | A | 11/1995 | Bader |
| 5,978,811 | A | 11/1999 | Smiley |
| 6,049,803 | A | 4/2000 | Szalwinski |
| 6,105,147 | A | 8/2000 | Molloy |
| 6,277,567 | B1 | 8/2001 | Graziosi |
| 6,528,260 | B1 | 3/2003 | Blumenfeld et al. |
| 6,570,567 | B1 | 5/2003 | Eaton |
| 6,886,015 | B2 | 4/2005 | Notargiacomo et al. |
| 6,950,753 | B1 | 9/2005 | Rzhetsky et al. |
| 7,957,907 | B2 | 6/2011 | Sorenson et al. |
| 8,185,557 | B2 | 5/2012 | Slinker |
| 8,224,821 | B2 | 7/2012 | Graham et al. |
| 8,510,057 | B1 | 8/2013 | Avey et al. |
| 8,738,297 | B2 | 5/2014 | Sorenson et al. |
| 8,855,935 | B2 | 10/2014 | Myres et al. |
| 9,116,882 | B1 | 8/2015 | Macpherson et al. |
| 9,213,947 | B1 | 12/2015 | Do et al. |
| 9,367,800 | B1 | 6/2016 | Do et al. |
| 9,836,576 | B1 | 12/2017 | Do et al. |
| 9,940,433 | B2 | 4/2018 | Han et al. |
| 10,025,877 | B2 | 7/2018 | Macpherson |
| 10,223,498 | B2 | 3/2019 | Han et al. |
| 11,238,957 | B2 | 2/2022 | Byrnes et al. |
| 2002/0143578 | A1 | 10/2002 | Cole et al. |
| 2003/0032015 | A1 | 2/2003 | Toivonen et al. |
| 2003/0113727 | A1 | 6/2003 | Girn et al. |
| 2003/0113756 | A1 | 6/2003 | Mertz |
| 2003/0172065 | A1 | 9/2003 | Sorenson et al. |
| 2003/0195707 | A1 | 10/2003 | Schork et al. |
| 2003/0204418 | A1 | 10/2003 | Ledley |
| 2004/0122705 | A1 | 6/2004 | Sabol et al. |
| 2004/0229231 | A1 | 11/2004 | Frudakis et al. |
| 2004/0243531 | A1 | 12/2004 | Dean |
| 2005/0147947 | A1 | 7/2005 | Cookson et al. |
| 2005/0149522 | A1 | 7/2005 | Cookson et al. |
| 2006/0020398 | A1 | 1/2006 | Vernon et al. |
| 2006/0136143 | A1 | 6/2006 | Avinash et al. |
| 2006/0161535 | A1 | 7/2006 | Holbrook |
| 2007/0037182 | A1 | 2/2007 | Gaskin et al. |
| 2008/0027656 | A1 | 1/2008 | Parida |
| 2008/0154566 | A1 | 6/2008 | Myres et al. |
| 2008/0228751 | A1 | 9/2008 | Kenedy et al. |
| 2008/0255768 | A1 | 10/2008 | Martin et al. |
| 2009/0100030 | A1 | 4/2009 | Isakson et al. |
| 2009/0299645 | A1 | 12/2009 | Colby et al. |
| 2010/0218228 | A1 | 8/2010 | Walter |
| 2011/0093448 | A1 | 4/2011 | Rafi et al. |
| 2011/0161168 | A1 | 6/2011 | Dubnicki |
| 2012/0218289 | A1 | 8/2012 | Rasmussen et al. |
| 2013/0085728 | A1 | 4/2013 | Tang et al. |
| 2013/0149707 | A1 | 6/2013 | Sorenson et al. |
| 2014/0067355 | A1 | 3/2014 | Noto et al. |
| 2014/0108527 | A1 | 4/2014 | Aravanis et al. |
| 2014/0278138 | A1 | 9/2014 | Barber et al. |
| 2015/0100243 | A1 | 4/2015 | Myres et al. |
| 2016/0350479 | A1 | 12/2016 | Han et al. |
| 2017/0011042 | A1 | 1/2017 | Kermany et al. |
| 2017/0277827 | A1 | 9/2017 | Granka et al. |
| 2017/0329891 | A1 | 11/2017 | Macpherson et al. |
| 2019/0034587 | A1 | 1/2019 | Anderson et al. |
| 2019/0147973 | A1 | 5/2019 | Han et al. |
| 2021/0057041 | A1 | 2/2021 | Byrnes et al. |

FOREIGN PATENT DOCUMENTS

| | | | |
|---|---|---|---|
| WO | WO 2016/073953 | A1 | 5/2016 |
| WO | WO 2016/193891 | A1 | 12/2016 |

OTHER PUBLICATIONS

Alexander, D.H., et al., "Fast model-based estimation of ancestry in unrelated individuals," Genome research, Sep. 2009, vol. 19, No. 9, pp. 1655-1664.

Atzmon, G. et al., "Abraham's Children in the Genome Era: Major Jewish Diaspora Populations Comprise Distinct Genetic Clusters with Shared Middle Eastern Ancestry," American Journal of Human Genetics 86(6), Jun. 11, 2010, pp. 850-859.

Belkin, M. et al., "Laplacian Eigenmaps for Dimensionality Reduction and Data Representation," Neural Computation 15, Jun. 2003, pp. 1373-1396.

Bengio, Y. et al., "Out-of-Sample Extensions for LLE, Isomap, MOS, Eigenmaps and Spectral Clustering," NIPS'03: Proceedings of the 16th International Conference on Neural Information Processing Systems, Dec. 2003, pp. 177-184.

Blondel, V.D. et al., "Fast Unfolding of Community Hierarchies in Large Networks," arXiv Preprint arXiv:0803.0476v1, Mar. 4, 2008, pp. 1-6.

Browning, B.L. et al., "Efficient Multilocus Association Testing for Whole Genome Association Studies Using Localized Haplotype Clustering," Genetic Epidemiology, 2007, Vo. 31, pp. 365-375.

Browning, S.R. et al., "High-resolution detection of Identity by Descent in unrelated individuals," The American Journal of Human Genetics, vol. 86, Apr. 9, 2010, pp. 526-539.

Browning, S.R. et al., "Rapid and Accurate Haplotype Phasing and Missing-Data Inference for Whole-Genome Association Studies by Use of Localized Haplotype Clustering," The American Journal of Human Genetics, Nov. 2007, pp. 1084-1096, vol. 81.

Browning, S.R., "Multilocus Association Mapping Using Variable-Length Markov Chains," The American Journal of Human Genetics, Jun. 2006, vol. 78, pp. 903-913.

Butler, John M., "Commonly Used Short Tandem Repeat Markers," Forensic DNA Typing, Chapter 5, 2001, pp. 53-54, Academic Press.

Cann, H.M. et al., "A human genome diversity cell line panel," Science, Apr. 2002, vol. 296, No. 5566, pp. 261-262.

Capocci, A., et al. "Detecting communities in large networks," Physica A: Statistical Mechanics and its Applications, vol. 352, Nos. 2-4, Jul. 15, 2005, 2005, pp. 669-676.

Carmi, S. et al., "Sequencing an Ashkenazi Reference Panel Supports Population-Targeted Personal Genomics and Illuminates Jewish and European Origins," Nature Communications 5:4835, Sep. 9, 2014, pp. 1-9.

Carmi, S. et al., "The Variance of Identity-by-Descent Sharing in the Wright-Fisher Model," Genetics 193(3), Mar. 2013, pp. 911-928.

Cavalli-Sforza, L.L. "The human genome diversity project: past, present and future," Nature Reviews Genetics, Apr. 2005, vol. 6, No. 4. pp. 333-340.

Coifman, R.R. et al., "Diffusion Maps," Applied and Computational Harmonic Analysis, vol. 21, No. 1, Jul. 2006, pp. 5-30.

Corach et al., "Mass disasters: Rapid molecular screening of human remains by means of short tandem repeats typing," Electrophoresis (1995) vol. 16, pp. 1617-1623.

Curtis, R.E. et al., "Estimation of recent ancestral origins of individuals on a large scale," KDD '17, Aug. 2017, pp. 1417-1425.

Durand, E.Y. et al., "Reducing Pervasive False-Positive Identical-by-Descent Segments Detected by Large-Scale Pedigree Analysis," Molecular Biology and Evolution 31(8), Apr. 30, 2014, pp. 2212-2222.

European Patent Office, Extended European Search Report and Opinion, EP Patent Application No. 19782160.6, dated Nov. 12, 2021, nine pages.

Falush, D. et al., "Inference of Population Structure Using Multilocus Genotype Data: Linked Loci and Correlated Allele Frequencies," Genetics Society of America, 2003, vol. 164, pp. 1567-1587.

Family Tree DNA. "Family Tree DNA." Family Tree DNA: Genealogy by Genetics, Ltd., Feb. 5, 2001, 2 pages, [Online] [Retrieved Aug. 1, 2023], Retrieved from the Internet Archive <URL:https://web.archive.org/web/20010205000900/http://www.familytreedna.com/main.html>.

Fortunato, S. et al., "Resolution Limit in Community Detection," Proceedings of the National Academy of Sciences 104(1), Jan. 2, 2007, pp. 36-41.

Fortunato, S., "Community Detection in Graphs," Physics Reports 486, No. 3-5, Feb. 2010, pp. 75-174.

Francioli, L. et al., "Whole-Genome Sequence Variation, Population Structure and Demographic History of the Dutch Population," Nature Genetics 46(8), Aug. 2014, pp. 818-825.

(56) References Cited

OTHER PUBLICATIONS

Gauvin, H. et al., "Genome-Wide Patterns of Identity-by-Descent Sharing in the French Canadian Founder Population," European Journal of Human Genetics 22, Oct. 16, 2013, pp. 814-821.
Genealogy Blog With Attitude, "Surnames, 23andMe, and AncestryDNA: Making the Most of Match Counts and "Enrichment"—Genealogy and Genomics," Apr. 4, 2015, 24 pages, [Online] Retrieved Jan. 23, 2019, Retrieved from the Internet: < URL: http://web.archive.org/web/20150404210843/https://ourpuzzlingpast.com/gene-blog/2015/01/25/surnames-23andme-and-ancestrydnamaking-the-most-of-match-counts-and-enrichment>.
Genealogy definition, Merriam-Webster Online Dictionary, 2004, http://www.mw.com/cqibin/dictionary?book=Dictionary&va=genealogy (1 page).
Girvan, M. et al., "Community Structure in Social and Biological Networks," PNAS 99(12), Jun. 11, 2002, pp. 7821-7826.
Good, B.H. et al., "Performance of Modularity Maximization in Practical Contexts," Physical Review E 81(4), Apr. 15, 2010, pp. 1-19.
Gusev, A. et al., "Whole Population, Genome-Wide Mapping of Hidden Relatedness," Genome Research, 2009, pp. 318-326, vol. 19.
Han, L. et al., "Identity by descent estimation with dense genome-wide genotype data," Genet Epidemiol., vol. 35, No. 6, Sep. 2011, pp. 557-567.
Hao, W. et al., "Probabilistic Models of Genetic Variation in Structured Populations Applied to Global Human Studies," arXiv:1312.2041, Dec. 7, 2013, pp. 1-35.
Jarvis, J.P. et al., "Patterns of Ancestry, Signatures of Natural Selection, and Genetic Association with Stature in Western African Pygmies," PLoS Genetics, 2012, vol. 8, No. 4, pp. 1-15.
King, T et al., "What's in a Name? Y Chromosomes, Surnames and the Genetic Genealogy Revolution," Trends in Genetics, 2009, pp. 351-360, vol. 25, No. 8.
Lee, A.B. et al., "A Spectral Graph Approach to Discovering Genetic Ancestry," Annals of Applied Statistics 4(1), Mar. 2010, pp. 179-202.
Lee, A.B. et al., "Discovering Genetic Ancestry Using Spectral Graph Theory," Genetic Epidemiology 34, May 19, 2009, pp. 51-59.
McGraw, P.N. et al., "Laplacian Spectra as a Diagnostic Tool for Network Structure and Dynamics," arXiv Preprint arXiv:0708.4206v1, Aug. 30, 2007, pp. 1-13.
McVean, G., "A Genealogical Interpretation of Principal Components Analysis," PLoS Genetics 5(10), Oct. 16, 2009, pp. 1-10.
Meirmans, P.G., "The Trouble with Isolation by Distance," Molecular Ecology 21(12), May 11, 2012, pp. 2839-2846.
Morrison, AC et al., "Prediction of Coronary Heart Disease Risk using a Genetic Risk Score: The Atherosclerosis Risk in Communities Study," American Journal of Epidemiology, 2007, vol. 166, No. 1, pp. 28-35.
Newman, M.E.J., "Communities, Modules and Large-Scale Structure in Networks," Nature Physics 8(1), Jan. 2012, pp. 25-31.
Noto, K. et al., "Underdog: A Fully-Supervised Phasing Algorithm That Learns from Hundreds of Thousands of Samples and Phases in Minutes," Oct. 20, 2014, 1 page.
Novembre, J. et al., "Genes Mirror Geography within Europe," Nature 456(7218), Nov. 2008, pp. 98-101.
Oxford Ancestors. "Oxford Ancestors: We Put the Genes in Genealogy." Oxfordancestors.com, Feb. 24, 2001, 3 pages, [Online] [Retrieved Aug. 1, 2023], Retrieved from the Internet Archive <URL:https://web.archive.org/web/20010224164734/http://www.oxfordancestors.com/>.
Palamara, P.F. et al., "Inference of Historical Migration Rates Via Haplotype Sharing," Bioinformatics 29(13), Jul. 2013, pp. 180-188.
Palamara, P.F. et al., "Length Distributions of Identity by Descent Reveal Fine-Scale Demographic History," American Journal of Human Genetics 91(5), Nov. 2, 2012, pp. 809-822.
Palin, K. et al., "Identity-by-Descent-Based Phasing and Imputation in Founder Populations Using Graphical Models," Genetic Epidemiology, vol. 35, Oct. 17, 2011, pp. 853-860.
Patterson, N. et al., "Population structure and eigenanalysis," PLoS genetics, Dec. 2006, vol. 2, No. 12, pp. 2074-2093.
PCT International Search Report and Written Opinion, International Application No. PCT/IB2019/052788, dated Aug. 9, 2019, eight pages.
PCT International Search Report and Written Opinion, PCT Application No. PCT/IB2016/053166, dated Sep. 6, 2016, 11 pages.
Platt, J.C. et al., "Probabilistic Outputs for Support Vector Machines and Comparisons to Regularized Likelihood Methods," Microsoft Research, Mar. 26, 1999, pp. 1-11.
Price, Al. et al., "Sensitive Detection of Chromosomal Segments of Distinct Ancestry in Admixed Populations," PLoS Genetics, 2009, vol. 5, No. 6, pp. 1-18.
Pritchard, J.K. et al., "Inference of population structure using multilocus genotype data," Genetics Society of America, Jun. 2000, vol. 155, No. 2, pp. 945-959.
Pugh, M. B. et al. "Stedman's Medical Dictionary." 27th Edition, 2000, p. 703.
Purcell, S. et al., "PLINK: A tool set for whole-genome association and population-based linkage analyses," The American Journal of Human Genetics, vol. 81, Sep. 2007, pp. 559-575.
Purcell, S., "Plink (1.07) Documentation," Harvard.edu, May 10, 2010, 293 pages, [Online] [Retrieved Oct. 14, 2024], Retrieved from the Internet <URL:http://zzz.bwh.harvard.edu/plink/dist/plink-doc-1.07.pdf.>.
Qian, Y. et al., "Efficient clustering of identity-by-descent between multiple individuals," Bioinformatics, vol. 30, No. 7, Dec. 19, 2013, pp. 915-922.
Rabiner, L.R. et al., "A Tutorial on hidden Markov Models and Selected Application in Speech Recognition," Proceedings of the IEEE, Feb. 1989, vol. 77, No. 2, pp. 257-286.
Raj, A. et al., "FastSTRUCTURE: Variational Inference of Population Structure in Large SNP Data Sets," Genetics 197(2), Jun. 2014, pp. 573-589.
Ron, D. et al., "On the Learnability and Usage of Acyclic Probabilistic Finite Automata," Journal of Computer and System Sciences, vol. 56, 1998, pp. 133-152.
Scheet, P. et al., "A Fast and Flexible Statistical Model for Large-Scale Population Genotype Data: Applications to Inferring Missing Genotypes and Haplotypic Phase," The American journal of Human Genetics, Apr. 2006, vol. 78, pp. 629-644.
Seligsohn, U. et al., "Genetic Susceptibility to Venous Thrombosis," The New England Journal of Medicine, Apr. 19, 2001, vol. 344, No. 16, pp. 1222-1231.
Staples, J. et al., "PRIMUS: Rapid Reconstruction of Pedigrees from Genome-wide Estimates of Identity by Descent," The American Journal of Human Genetics, vol. 95, Nov. 6, 2014, pp. 553-564.
Stevens, E. L., et al., "Inference of Relationships in Population Data Using Identity-by-Descent," PLOS Genetics, vol. 7, Iss. 9, Sep. 22, 2011, pp. 1-15.
Sundquist, A et al., "Effect of genetic divergence in identifying ancestral origin using HAPPA," Genome Research, 2008, Vo. 18, 8 pages.
The 1000 Genomes Project Consortium, "An Integrated Map of Genetic Variation from 1,092 Human Genomes," Nature 491, Nov. 2012, pp. 56-65.
The International Hapmap 3 Consortium. "Integrating common and rare genetic variation in diverse human populations," Nature, Sep. 2, 2010, vol. 467, pp. 52-58.
The International Hapmap Consortium, "A haplotype map of the human genome," Nature, Oct. 2005, vol. 437, No. 27, pp. 1299-1320.
The International Hapmap Consortium, "A second generation human haplotype map of over 3.1 million SNPs," Nature, Oct. 2007, vol. 449, No. 7164, pp. 1-30.
Tipping, M.E., "Sparse Bayesian Learning and the Relevance Vector Machine," Journal of Machine Learning Research, 2001, vol. 1, pp. 211-244.
Von Luxburg, U., "A Tutorial on Spectral Clustering," Statistics and Computing 17(4), Aug. 22, 2007, pp. 1-32.
Weedon, M.N. et al., "Combining Information from Common Type 2 Diabetes Risk Polymorphisms Improves Disease Prediction," PLoS Medicine, Oct. 2006, vol. 3, No. 10, pp. 1877-1882.

(56) References Cited

OTHER PUBLICATIONS

Welch, B.L., "The Generalization of "Student's" Problem when Several Different Population Variances are Involved," Biometrika 34(1-2), 1947, pp. 28-35.

Wikipedia, "Identity by descent," Wikipedia: The Free Encyclopedia, Feb. 13, 2015, 5 pages, [Online] [Retrieved Oct. 14, 2024], Retrieved from the Internet <URL:https://en.wikipedia.org/w/index.php?title=Identity_by_descent&oldid=646873616>.

Williams, A.L. et al., "Phasing of Many Thousands of Genotyped Samples," The American Journal of Human Genetics, Aug. 10, 2012, vol. 91, pp. 238-251.

Wilson et al., "Genealogical Inference from Microsatellite Data," Genetics (1998) 150:499-510.

Yang, Q. et al., "Improving the Prediction of Complex Diseases by Testing for Multiple Disease—Susceptibility Genes," American Journal of Human Genetics, 2003, vol. 72, pp. 636-649.

Yoon, B.J., "Hidden Markov Models and their Applications in Biological Sequence Analysis," Current Genomics, 2009, vol. 10, pp. 402-415.

Zelnik-Manor, L. et al., "Self-Tuning Spectral Clustering," In Advances in Neural Information Processing Systems 17, Jan. 2004, pp. 1601-1608.

Zhang, J., "Ancestral Informative Marker Selection and Population Structure Visualization Using Sparse Laplacian Eigenfunctions," PLoS One 5(11), Nov. 4, 2010, pp. 1-12.

Zhao, F. et al., "Spectral Clustering with Eigenvector Selection Based on Entropy Ranking," Neurocomputing 73(10-12), Mar. 12, 2010, pp. 1704-1717.

\* cited by examiner

DETERMINATION OF DATA-SOURCE INFLUENCE ON DATA MANIFESTATIONS

CROSS-REFERENCE TO RELATED APPLICATION

The present application claims the benefit of U.S. Provisional Patent Application No. 63/511,084 filed on Jun. 29, 2023, which is hereby incorporated by reference in its entirety.

FIELD

The disclosed embodiments relate to determining influences of data sources on data manifestations.

BACKGROUND

Data-inheritance origins may be referred to as origins and describe how data may be inherited from real-world events. Data may be inherited and evolved based on real-world events that are not always recorded or documented. Yet, while the real-world events may not be completely documented, the change and inheritance of those events may be traceable by comparing data strings among data instances. For example, two data instances may be generated independently and individually reflect the status of their respective named entities or events. The data patterns in the data instances may reflect the natures, histories, or characteristics of data inheritance sources such as related or unrelated named entities or events. However, multiple data instances or corresponding named entities or events may be inherited from one or more common sources so that the data instances share some similarities in the data pattern. As such, the nature of inheritance may be revealed by analyzing and comparing the multiple data instances, and sometimes a large number of data instances. Those real-life events that result in shared data strings among data instances may be referred to as data inheritance events, even though those real-life events, at the time of the occurrence, may not involve data or data generation at all. For example, the real-life events may be historical events that occurred before the invention of computers or data but present data instances may still reflect those historical events.

SUMMARY

Disclosed herein relates to example embodiments that predict data-source influences on one or more data manifestations of a named entity. The method includes receiving an inheritance dataset of the named entity, the inheritance dataset including one or more reads at a plurality of data-bit regions. The method determines first and second portions of the inheritance dataset of the named entity. The first portion is associated with a first data source. The second portion is associated with a second data source. The method determines an aggregated data-bit association score for the named entity based on the inheritance dataset at an identified subset of the data-bit regions. The method determines an aggregated data-bit association score associated with the first data source based on the first portion of the inheritance dataset at the identified subset of the data-bit regions. The method determines an aggregated data-bit association score associated with the second data source based on the second portion of the inheritance dataset at the identified subset of the data-bit regions. Based on the aggregated data-bit association scores associated with the named entity, the method selects one of the first and second data sources as having a measure of influence on a data manifestation of the named entity corresponding to the identified subset of the data-bit regions.

In yet another embodiment, a non-transitory computer-readable medium that is configured to store instructions is described. The instructions, when executed by one or more processors, cause the one or more processors to perform a process that includes steps described in the above computer-implemented methods or described in any embodiments of this disclosure. In yet another embodiment, a system may include one or more processors and a storage medium that is configured to store instructions. The instructions, when executed by one or more processors, cause the one or more processors to perform a process that includes steps described in the above computer-implemented methods or described in any embodiments of this disclosure.

The figures depict various embodiments for purposes of illustration only. One skilled in the art will readily recognize from the following discussion that alternative embodiments of the structures and methods illustrated herein may be employed without departing from the principles described herein.

DETAILED DESCRIPTION

The figures (FIGs.) and the following description relate to preferred embodiments by way of illustration only. One of skill in the art may recognize alternative embodiments of the structures and methods disclosed herein as viable alternatives that may be employed without departing from the principles of what is disclosed.

Reference will now be made in detail to several embodiments, examples of which are illustrated in the accompanying figures. It is noted that wherever practicable similar or like reference numbers may be used in the figures and may indicate similar or like functionality. The figures depict embodiments of the disclosed system (or method) for purposes of illustration only. One skilled in the art will readily recognize from the following description that alternative embodiments of the structures and methods illustrated herein may be employed without departing from the principles described herein.

Example System Environment

Figure 1:
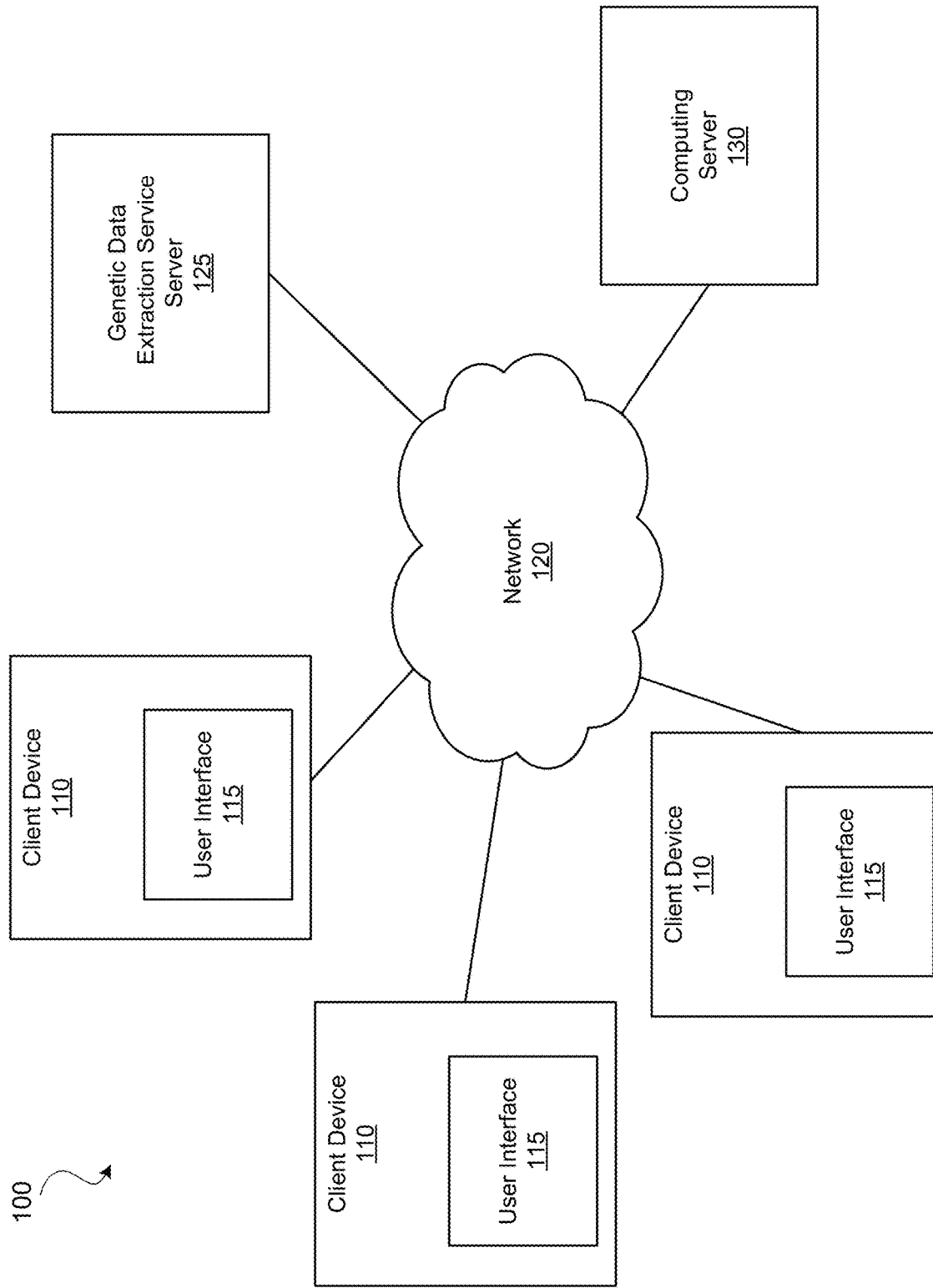
FIG. 1 illustrates a diagram of a system environment of an example computing system, in accordance with some embodiments.

FIG. 1 illustrates a diagram of a system environment 100 of an example computing server 130, in accordance with some embodiments. The system environment 100 shown in FIG. 1 includes one or more client devices 110, a network 120, a genetic data extraction service server 125, and a computing server 130. In various embodiments, the system environment 100 may include fewer or additional components. The system environment 100 may also include different components.

The client devices 110 are one or more computing devices capable of receiving user input as well as transmitting and/or receiving data via a network 120. Example computing devices include desktop computers, laptop computers, personal digital assistants (PDAs), smartphones, tablets, wearable electronic devices (e.g., smartwatches), smart household appliances (e.g., smart televisions, smart speakers, smart home hubs), Internet of Things (IoT) devices or other suitable electronic devices. A client device 110 communicates to other components via the network 120. Users may be customers of the computing server 130 or any individuals who access the system of the computing server 130, such as an online website or a mobile application. In some embodiments, a client device 110 executes an application that launches a graphical user interface (GUI) for a user of the client device 110 to interact with the computing server 130. The GUI may be an example of a user interface 115. A client device 110 may also execute a web browser application to enable interactions between the client device 110 and the computing server 130 via the network 120. In another embodiment, the user interface 115 may take the form of a software application published by the computing server 130 and installed on the user device 110. In yet another embodiment, a client device 110 interacts with the computing server 130 through an application programming interface (API) running on a native operating system of the client device 110, such as IOS or ANDROID.

The network 120 provides connections to the components of the system environment 100 through one or more sub-networks, which may include any combination of local area and/or wide area networks, using both wired and/or wireless communication systems. In some embodiments, a network 120 uses standard communications technologies and/or protocols. For example, a network 120 may include communication links using technologies such as Ethernet, 802.11, worldwide interoperability for microwave access (WiMAX), 3G, 4G, Long Term Evolution (LTE), 5G, code division multiple access (CDMA), digital subscriber line (DSL), etc. Examples of network protocols used for communicating via the network 120 include multiprotocol label switching (MPLS), transmission control protocol/Internet protocol (TCP/IP), hypertext transport protocol (HTTP), simple mail transfer protocol (SMTP), and file transfer protocol (FTP). Data exchanged over a network 120 may be represented using any suitable format, such as hypertext markup language (HTML) or extensible markup language (XML). In some embodiments, all or some of the communication links of a network 120 may be encrypted using any suitable technique or techniques such as secure sockets layer (SSL), transport layer security (TLS), virtual private networks (VPNs), Internet Protocol security (IPsec), etc. The network 120 also includes links and packet-switching networks such as the Internet.

Individuals, who may be customers of a company operating the computing server 130, provide biological samples for analysis of their genetic data. Individuals may also be referred to as users. In some embodiments, an individual uses a sample collection kit to provide a biological sample (e.g., saliva, blood, hair, tissue) from which genetic data is extracted and determined according to nucleotide processing techniques such as microarray, amplification and/or sequencing. Microarray may include immobilizing probe DNA sequences, onto a solid surface such as a glass slide. Target DNA samples, labeled with fluorescent tags, are then applied to the microarray surface. Through complementary base pairing, the labeled DNA binds to its corresponding probe on the microarray. By detecting the fluorescence emitted by the labeled DNA, genetic data may be extracted. Amplification may include using polymerase chain reaction (PCR) to amplify segments of nucleotide samples. Sequencing may include sequencing of deoxyribonucleic acid (DNA) sequencing, ribonucleic acid (RNA) sequencing, etc. Suitable sequencing techniques may include Sanger sequencing and massively parallel sequencing such as various next-generation sequencing (NGS) techniques including whole genome sequencing, pyrosequencing, sequencing by synthesis, sequencing by ligation, and ion semiconductor sequencing. In some embodiments, a set of SNPs (e.g., 300,000) that are shared between different array platforms (e.g., Illumina OmniExpress Platform and Illumina Human-Hap 650Y Platform) may be obtained as genetic data. Genetic data extraction service server 125 receives biological samples from users of the computing server 130. The genetic data extraction service server 125 extracts genetic data from the samples and the data may take the form of a set of SNPs. The genetic data extraction service server 125 generates the genetic data of the individuals based on sequencing or microarray results. The genetic data may include data generated from DNA or RNA and may include base pairs from coding and/or noncoding regions of DNA.

The genetic data may take different forms and include information regarding various biomarkers of an individual. For example, in some embodiments, the genetic data may be the base pair sequence of an individual. The base pair sequence may include the whole genome or a part of the genome such as certain genetic loci of interest. In another embodiment, the genetic data extraction service server 125 may determine genotypes from DNA identification results, for example by identifying genotype values of single nucleotide polymorphisms (SNPs) present within the DNA. The results in this example may include a sequence of genotypes corresponding to various SNP sites. A SNP site may also be referred to as a SNP locus. A genetic locus is a segment of a genetic sequence. A locus can be a single site or a longer stretch. The segment can be a single base long or multiple bases long. In some embodiments, the genetic data extraction service server 125 may perform data pre-processing of the genetic data to convert raw sequences of base pairs to sequences of genotypes at or genotyping data of target SNP sites. Since a typical human genome may differ from a reference human genome at only several million SNP sites (as opposed to billions of base pairs in the whole genome), the genetic data extraction service server 125 may extract only the genotypes at or genotyping data of a set of target SNP sites and transmit the extracted data to the computing server 130 as the inheritance dataset of an individual. SNPs, base pair sequences, genotypes, haplotypes, RNA sequences, protein sequences, and phenotypes are examples of biomarkers. In some embodiments, each SNP site may have two readings that are heterozygous.

The computing server 130 performs various analyses of the genetic data, genealogy data, and users' survey responses to generate results regarding the phenotypes and genealogy of users of computing server 130. Depending on the embodiments, the computing server 130 may also be referred to as an online server, a personal genetic service server, a genealogy server, a family tree building server, and/or a social networking system. The computing server 130 receives genetic data from the genetic data extraction service server 125 and stores the genetic data in the data store of the computing server 130. The computing server 130 may analyze the data to generate results regarding the genetics or genealogy of users. The results regarding the genetics or genealogy of users may include the ethnicity compositions of users, paternal and maternal genetic analysis, identification or suggestion of potential family relatives, ancestor information, analyses of DNA data, potential or identified traits such as phenotypes of users (e.g., diseases, appearance traits, other genetic characteristics, and other non-genetic characteristics including social characteristics), etc. The computing server 130 may present or cause the user interface 115 to present the results to the users through a GUI displayed on the client device 110. The results may include graphical elements, textual information, data, charts, and other elements such as family trees.

In some embodiments, the computing server 130 also allows various users to create one or more genealogical profiles of the user. The genealogical profile may include a list of individuals (e.g., ancestors, relatives, friends, and other people of interest) who are added or selected by the user or suggested by the computing server 130 based on the genealogical records and/or genetic records. The user interface 115 controlled by or in communication with the computing server 130 may display the individuals in a list or as a family tree such as in the form of a pedigree chart. In some embodiments, subject to the user's privacy setting and authorization, the computing server 130 may allow information generated from the user's inheritance dataset to be linked to the user profile and to one or more of the family trees. The users may also authorize the computing server 130 to analyze their inheritance dataset and allow their profiles to be discovered by other users.

Example Computing Server Architecture

Figure 2:
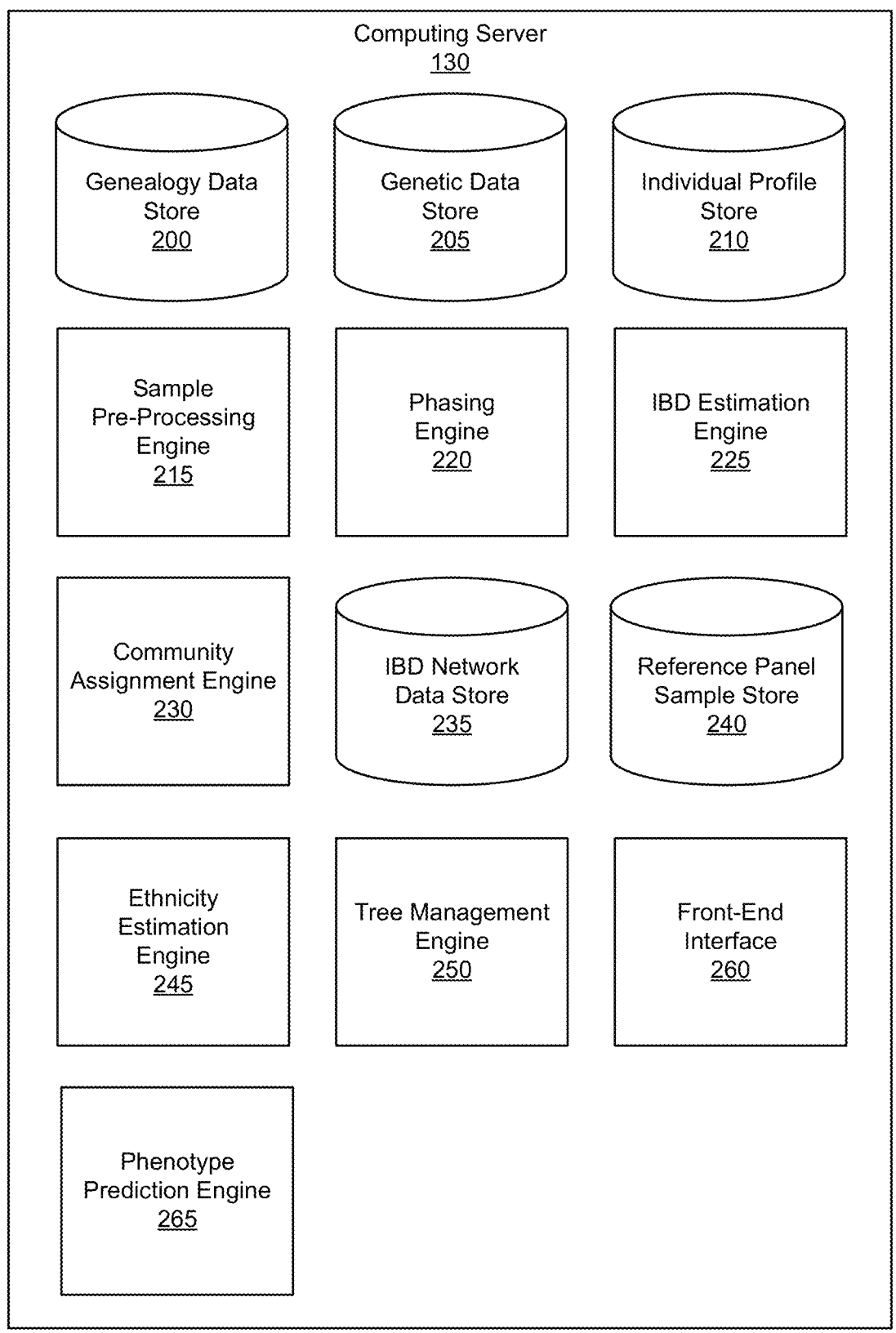
FIG. 2 is a block diagram of an architecture of an example computing system, in accordance with some embodiments.

FIG. 2 is a block diagram of the architecture of an example computing server 130, in accordance with some embodiments. In the embodiment shown in FIG. 2, the computing server 130 includes a genealogy data store 200, a genetic data store 205, an individual profile store 210, a sample pre-processing engine 215, a phasing engine 220, an identity by descent (IBD) estimation engine 225, a community assignment engine 230, an IBD network data store 235, a reference panel sample store 240, an ethnicity estimation engine 245, a front-end interface 260, and a tree management engine 250. The functions of the computing server 130 may be distributed among the elements in a different manner than described. In various embodiments, the computing server 130 may include different components and fewer or additional components. Each of the various data stores may be a single storage device, a server controlling multiple storage devices, or a distributed network that is accessible through multiple nodes (e.g., a cloud storage system).

The computing server 130 stores various data of different individuals, including genetic data, genealogy data, and survey response data. The computing server 130 processes the genetic data of users to identify shared identity-by-descent (IBD) segments between individuals. The genealogy data and survey response data may be part of user profile data. The amount and type of user profile data stored for each user may vary based on the information of a user, which is provided by the user as she creates an account and profile at a system operated by the computing server 130 and continues to build her profile, family tree, and social network at the system and to link her profile with her genetic data. Users may provide data via the user interface 115 of a client device 110. Initially and as a user continues to build her genealogical profile, the user may be prompted to answer questions related to the basic information of the user (e.g., name, date of birth, birthplace, etc.) and later on more advanced questions that may be useful for obtaining additional genealogy data. The computing server 130 may also include survey questions regarding various traits of the users such as the users' phenotypes, characteristics, preferences, habits, lifestyle, environment, etc.

Genealogy data may be stored in the genealogy data store 200 and may include various types of data that are related to tracing family relatives of users. Examples of genealogy data include names (first, last, middle, suffixes), gender, birth locations, date of birth, date of death, marriage information, spouse's information kinships, family history, dates and places for life events (e.g., birth and death), other vital data, and the like. In some instances, family history can take the form of a pedigree of an individual (e.g., the recorded relationships in the family). The family tree information associated with an individual may include one or more specified nodes. Each node in the family tree represents the individual, an ancestor of the individual who might have passed down genetic material to the individual, and the individual's other relatives including siblings, cousins, and offspring in some cases. Genealogy data may also include connections and relationships among users of the computing server 130. The information related to the connections between a user and her relatives that may be associated with a family tree may also be referred to as pedigree data or family tree data.

In addition to user-input data, genealogy data may also take other forms that are obtained from various sources such as public records and third-party data collectors. For example, genealogical records from public sources include birth records, marriage records, death records, census records, court records, probate records, adoption records, obituary records, etc. Likewise, genealogy data may include data from one or more family trees of an individual, the Ancestry World Tree system, a Social Security Death Index database, the World Family Tree system, a birth certificate database, a death certificate database, a marriage certificate database, an adoption database, a draft registration database, a veterans database, a military database, a property records database, a census database, a voter registration database, a phone database, an address database, a newspaper database, an immigration database, a family history records database, a local history records database, a business registration database, a motor vehicle database, and the like.

Furthermore, the genealogy data store 200 may also include relationship information inferred from the genetic data stored in the genetic data store 205 and information received from the individuals. For example, the relationship information may indicate which individuals are genetically related, how they are related, how many generations back they share common ancestors, lengths and locations of IBD segments shared, which genetic communities an individual is a part of by the individual, and the like.

The computing server 130 maintains inheritance datasets of individuals in the genetic data store 205. An inheritance dataset of an individual may be a digital dataset of nucleotide data (e.g., SNP data) and corresponding metadata. For example, an inheritance dataset may be genetic data extracted by the genetic data extraction service server 125. An inheritance dataset may contain data on the whole or portions of an individual's genome. The genetic data store 205 may store a pointer to a location associated with the genealogy data store 200 associated with the individual. An inheritance dataset may take different forms. In some embodiments, an inheritance dataset may take the form of a base pair sequence of the sequencing result of an individual. A base pair sequence dataset may include the whole genome of the individual (e.g., obtained from a whole-genome sequencing) or some parts of the genome (e.g., genetic loci of interest). A microarray data may take the form of SNP data at target positions in the genome.

In another embodiment, an inheritance dataset may take the form of sequences of genetic markers. Examples of genetic markers may include target SNP sites (e.g., allele sites) filtered from the DNA identification results. A SNP site that is a single base pair long may also be referred to as a SNP locus. A SNP site may be associated with a unique identifier. The inheritance dataset may be in the form of diploid data that includes a sequence of genotypes, such as genotypes at or genotyping data of the target SNP site, or the whole base pair sequence that includes genotypes at or genotyping data of known SNP sites and other base pair sites that are not commonly associated with known SNPs. The diploid dataset may be referred to as a genotype dataset or a genotype sequence. Genotype may have a different meaning in various contexts. In one context, an individual's genotype may refer to a collection of diploid alleles of an individual. In other contexts, a genotype may be a pair of alleles present on two chromosomes for an individual at a given genetic marker such as a SNP site.

Genotype data for a SNP site may include a pair of alleles. The pair of alleles may be homozygous (e.g., A-A or G-G) or heterozygous (e.g., A-T, C-T). Instead of storing the actual nucleotides, the genetic data store 205 may store genetic data that are converted to bits. For a given SNP site, oftentimes only two nucleotide alleles (instead of all 4) are observed. As such, a 2-bit number may represent a SNP site. For example, 00 may represent homozygous first alleles, 11 may represent homozygous second alleles, and 01 or 10 may represent heterozygous alleles. A separate library may store what nucleotide corresponds to the first allele and what nucleotide corresponds to the second allele at a given SNP site.

A diploid dataset may also be phased into two sets of haploid data, one corresponding to a first parent side and another corresponding to a second parent side. The phased datasets may be referred to as haplotype datasets or haplotype sequences. Similar to genotype, haplotype may have a different meaning in various contexts. In one context, a haplotype may also refer to a collection of alleles that corresponds to a genetic segment. In other contexts, a haplotype may refer to a specific allele at a SNP site. For example, a sequence of haplotypes may refer to a sequence of alleles of an individual that are inherited from a parent.

The individual profile store 210 stores profiles and related metadata associated with various individuals appeared in the computing server 130. A computing server 130 may use unique individual identifiers to identify various users and other non-users that might appear in other data sources such as ancestors or historical persons who appear in any family tree or genealogy database. A unique individual identifier may be a hash of certain identification information of an individual, such as a user's account name, user's name, date of birth, location of birth, or any suitable combination of the information. The profile data related to an individual may be stored as metadata associated with an individual's profile. For example, the unique individual identifier and the metadata may be stored as a key-value pair using the unique individual identifier as a key.

An individual's profile data may include various kinds of information related to the individual. The metadata about the individual may include one or more pointers associating inheritance datasets such as genotype and phased haplotype data of the individual that are saved in the genetic data store 205. The metadata about the individual may also be individual information related to family trees and pedigree datasets that include the individual. The profile data may further include declarative information about the user that was authorized by the user to be shared and may also include information inferred by the computing server 130. Other examples of information stored in a user profile may include biographic, demographic, and other types of descriptive information such as work experience, educational history, gender, hobbies, preferences, location and the like. In some embodiments, the user profile data may also include one or more photos of the users and photos of relatives (e.g., ancestors) of the users that are uploaded by the users. A user may authorize the computing server 130 to analyze one or more photos to extract information, such as the user's or relative's appearance traits (e.g., blue eyes, curved hair, etc.), from the photos. The appearance traits and other information extracted from the photos may also be saved in the profile store. In some cases, the computing server may allow users to upload many different photos of the users, their relatives, and even friends. User profile data may also be obtained from other suitable sources, including historical records (e.g., records related to an ancestor), medical records, military records, photographs, other records indicating one or more traits, and other suitable recorded data.

For example, the computing server 130 may present various survey questions to its users from time to time. The responses to the survey questions may be stored at individual profile store 210. The survey questions may be related to various aspects of the users and the users' families. Some survey questions may be related to users' phenotypes, while other questions may be related to the environmental factors of the users.

Survey questions may concern health or disease-related phenotypes, such as questions related to the presence or absence of genetic diseases or disorders, inheritable diseases or disorders, or other common diseases or disorders that have a family history as one of the risk factors, questions regarding any diagnosis of increased risk of any diseases or disorders, and questions concerning wellness-related issues such as a family history of obesity, family history of causes of death, etc. The diseases identified by the survey questions may be related to single-gene diseases or disorders that are caused by a single-nucleotide variant, an insertion, or a deletion. The diseases identified by the survey questions may also be multifactorial inheritance disorders that may be caused by a combination of environmental factors and genes. Examples of multifactorial inheritance disorders may include heart disease, Alzheimer's disease, diabetes, cancer, and obesity. The computing server 130 may obtain data on a user's disease-related phenotypes from survey questions about the health history of the user and her family and also from health records uploaded by the user.

Survey questions also may be related to other types of phenotypes such as appearance traits of the users. A survey regarding appearance traits and characteristics may include questions related to eye color, iris pattern, freckles, chin types, finger length, dimple chin, earlobe types, hair color, hair curl, skin pigmentation, susceptibility to skin burn, bitter taste, male baldness, baldness pattern, presence of unibrow, presence of wisdom teeth, height, and weight. A survey regarding other traits also may include questions related to users' taste and smell such as the ability to taste bitterness, asparagus smell, cilantro aversion, etc. A survey regarding traits may further include questions related to users' body conditions such as lactose tolerance, caffeine consumption, malaria resistance, norovirus resistance, muscle performance, alcohol flush, etc. Other survey questions regarding a person's physiological or psychological traits may include vitamin traits and sensory traits such as the ability to sense an asparagus metabolite. Traits may also be collected from historical records, electronic health records and electronic medical records.

The computing server 130 also may present various survey questions related to the environmental factors of users. In this context, an environmental factor may be a factor that is not directly connected to the genetics of the users. Environmental factors may include users' preferences, habits, and lifestyles. For example, a survey regarding users' preferences may include questions related to things and activities that users like or dislike, such as types of music a user enjoys, dancing preference, party-going preference, certain sports that a user plays, video game preferences, etc. Other questions may be related to the users' diet preferences such as like or dislike a certain type of food (e.g., ice cream, egg). A survey related to habits and lifestyle may include questions regarding smoking habits, alcohol consumption and frequency, daily exercise duration, sleeping habits (e.g., morning person versus night person), sleeping cycles and problems, hobbies, and travel preferences. Additional environmental factors may include diet amount (calories, macronutrients), physical fitness abilities (e.g., stretching, flexibility, heart rate recovery), family type (adopted family or not, has siblings or not, lived with extended family during childhood), property and item ownership (has home or rents, has a smartphone or doesn't, has a car or doesn't).

Surveys also may be related to other environmental factors such as geographical, social-economic, or cultural factors. Geographical questions may include questions related to the birth location, family migration history, town, or city of users' current or past residence. Social-economic questions may be related to users' education level, income, occupations, self-identified demographic groups, etc. Questions related to culture may concern users' native language, language spoken at home, customs, dietary practices, etc. Other questions related to users' cultural and behavioral questions are also possible.

For any survey questions asked, the computing server 130 may also ask an individual the same or similar questions regarding the traits and environmental factors of the ancestors, family members, other relatives or friends of the individual. For example, a user may be asked about the native language of the user and the native languages of the user's parents and grandparents. A user may also be asked about the health history of his or her family members.

In addition to storing the survey data in the individual profile store 210, the computing server 130 may store some responses that correspond to data related to genealogical and genetics respectively to genealogy data store 200 and genetic data store 205.

The user profile data, photos of users, survey response data, the genetic data, and the genealogy data may be subject to the privacy and authorization setting of the users to specify any data related to the users that can be accessed, stored, obtained, or otherwise used. For example, when presented with a survey question, a user may select to answer or skip the question. The computing server 130 may present users from time to time information regarding users' selection of the extent of information and data shared. The computing server 130 also may maintain and enforce one or more privacy settings for users in connection with the access of the user profile data, photos, genetic data, and other sensitive data. For example, the user may pre-authorize the access to the data and may change the setting as wished. The privacy settings also may allow a user to specify (e.g., by opting out, by not opting in) whether the computing server 130 may receive, collect, log, or store particular data associated with the user for any purpose. A user may restrict her data at various levels. For example, on one level, the data may not be accessed by the computing server 130 for purposes other than displaying the data in the user's own profile. On another level, the user may authorize anonymization of her data and participate in studies and research conducted by the computing server 130 such as a large-scale genetic study. On yet another level, the user may turn some portions of her genealogy data public to allow the user to be discovered by other users (e.g., potential relatives) and be connected to one or more family trees. Access or sharing of any information or data in the computing server 130 may also be subject to one or more similar privacy policies. A user's data and content objects in the computing server 130 may also be associated with different levels of restriction. The computing server 130 may also provide various notification features to inform and remind users of their privacy and access settings. For example, when privacy settings for a data entry allow a particular user or other entities to access the data, the data may be described as being "visible," "public," or other suitable labels, contrary to a "private" label.

In some cases, the computing server 130 may have heightened privacy protection on certain types of data and data related to certain vulnerable groups. In some cases, the heightened privacy settings may strictly prohibit the use, analysis, and sharing of data related to a certain vulnerable group. In other cases, the heightened privacy settings may specify that data subject to those settings require prior approval for access, publication, or other use. In some cases, the computing server 130 may provide heightened privacy as a default setting for certain types of data, such as genetic data or any data that the user marks as sensitive. The user may opt in to sharing those data or change the default privacy settings. In other cases, the heightened privacy settings may apply across the board for all data of certain groups of users. For example, if computing server 130 determines that the user is a minor or has recognized that a picture of a minor is uploaded, the computing server 130 may designate all profile data associated with the minor as sensitive. In those cases, the computing server 130 may have one or more extra steps in seeking and confirming any sharing or use of the sensitive data.

In some embodiments, the individual profile store 210 may be a large-scale data store. In some embodiments, the individual profile store 210 may include at least 10,000 data records in the form of user profiles and each user profile may be associated with one or more inheritance datasets and one or more genealogical data entries. In some embodiments, the individual profile store 210 may include at least 50,000 data records in the form of user profiles and each user profile may be associated with one or more inheritance datasets and one or more genealogical data entries. In some embodiments, the individual profile store 210 may include at least 100,000 data records in the form of user profiles and each user profile may be associated with one or more inheritance datasets and one or more genealogical data entries. In some embodiments, the individual profile store 210 may include at least 500,000 data records in the form of user profiles and each user profile may be associated with one or more inheritance datasets and one or more genealogical data entries. In some embodiments, the individual profile store 210 may include at least 1,000,000 data records in the form of user profiles and each user profile may be associated with one or more inheritance datasets and one or more genealogical data entries. In some embodiments, the individual profile store 210 may include at least 2,000,000 data records in the form of user profiles and each user profile may be associated with one or more inheritance datasets and one or more genealogical data entries. In some embodiments, the individual profile store 210 may include at least 5,000,000 data records in the form of user profiles and each user profile may be associated with one or more inheritance datasets and one or more genealogical data entries. In some embodiments, the individual profile store 210 may include at least 10,000,000 data records in the form of user profiles and each user profile may be associated with one or more inheritance datasets and one or more genealogical data entries.

The sample pre-processing engine 215 receives and pre-processes data received from various sources to change the data into a format used by the computing server 130. For genealogy data, the sample pre-processing engine 215 may receive data from an individual via the user interface 115 of the client device 110. To collect the user data (e.g., genealogical and survey data), the computing server 130 may cause an interactive user interface on the client device 110 to display interface elements in which users can provide genealogy data and survey data. Additional data may be obtained from scans of public records. The data may be manually provided or automatically extracted via, for example, optical character recognition (OCR) performed on census records, town or government records, or any other item of printed or online material. Some records may be obtained by digitalizing written records such as older census records, birth certificates, death certificates, etc.

The sample pre-processing engine 215 may also receive raw data from the genetic data extraction service server 125. The genetic data extraction service server 125 may perform laboratory analysis of biological samples of users and generate sequencing results in the form of digital data. The sample pre-processing engine 215 may receive the raw inheritance datasets from the genetic data extraction service server 125. Most of the mutations that are passed down to descendants are related to single-nucleotide polymorphism (SNP). SNP is a substitution of a single nucleotide that occurs at a specific position in the genome. The sample pre-processing engine 215 may convert the raw base pair sequence into a sequence of genotypes of target SNP sites. Alternatively, the pre-processing of this conversion may be performed by the genetic data extraction service server 125. The sample pre-processing engine 215 identifies autosomal SNPs in an individual's inheritance dataset. In some embodiments, the SNPs may be autosomal SNPs. In some embodiments, 700,000 SNPs may be identified in an individual's data and may be stored in genetic data store 205. Alternatively, in some embodiments, an inheritance dataset may include at least 10,000 SNP sites. In another embodiment, an inheritance dataset may include at least 100,000 SNP sites. In yet another embodiment, an inheritance dataset may include at least 300,000 SNP sites. In yet another embodiment, an inheritance dataset may include at least 1,000,000 SNP sites. The sample pre-processing engine 215 may also convert the nucleotides into bits. The identified SNPs, in bits or in other suitable formats, may be provided to the phasing engine 220 which phases the individual's diploid genotypes to generate a pair of haplotypes for each user.

The phasing engine 220 phases a diploid inheritance dataset into a pair of haploid inheritance datasets and may perform imputation of SNP values at certain sites whose alleles are missing. An individual's haplotype may refer to a collection of alleles (e.g., a sequence of alleles) that are inherited from a parent.

Phasing may include a process of determining the assignment of alleles (particularly heterozygous alleles) to chromosomes. Owing to conditions and other constraints in sequencing or microarray, a DNA identification result often includes data regarding a pair of alleles at a given SNP locus of a pair of chromosomes but may not be able to distinguish which allele belongs to which specific chromosome. The phasing engine 220 uses a genotype phasing algorithm to assign one allele to a first chromosome and another allele to another chromosome. The genotype phasing algorithm may be developed based on an assumption of linkage disequilibrium (LD), which states that haplotype in the form of a sequence of alleles tends to cluster together. The phasing engine 220 is configured to generate phased sequences that are also commonly observed in many other samples. Put differently, haplotype sequences of different individuals tend to cluster together. A haplotype-cluster model may be generated to determine the probability distribution of a haplotype that includes a sequence of alleles. The haplotype-cluster model may be trained based on labeled data that includes known phased haplotypes from a trio (parents and a child). A trio is used as a training sample because the correct phasing of the child is almost certain by comparing the child's genotypes to the parent's inheritance datasets. The haplotype-cluster model may be generated iteratively along with the phasing process with a large number of unphased genotype datasets. The haplotype-cluster model may also be used to impute one or more missing data.

By way of example, the phasing engine 220 may use a directed acyclic graph model such as a hidden Markov model (HMM) to perform the phasing of a target genotype dataset. The directed acyclic graph may include multiple levels, each level having multiple nodes representing different possibilities of haplotype clusters. An emission probability of a node, which may represent the probability of having a particular haplotype cluster given an observation of the genotypes may be determined based on the probability distribution of the haplotype-cluster model. A transition probability from one node to another may be initially assigned to a non-zero value and be adjusted as the directed acyclic graph model and the haplotype-cluster model are trained. Various paths are possible in traversing different levels of the directed acyclic graph model. The phasing engine 220 determines a statistically likely path, such as the most probable path or a probable path that is at least more likely than 95% of other possible paths, based on the transition probabilities and the emission probabilities. A suitable dynamic programming algorithm such as the Viterbi algorithm may be used to determine the path. The determined path may represent the phasing result. U.S. Pat. No. 10,679,729, entitled "Haplotype Phasing Models," granted on Jun. 9, 2020, describes example embodiments of haplotype phasing.

A phasing algorithm may also generate phasing result that has a long genomic distance accuracy and cross-chromosome accuracy in terms of haplotype separation. For example, in some embodiments, an IBD-phasing algorithm may be used, which is described in further detail in U.S. Patent Application Publication No. US 2021/0034647, entitled "Clustering of Matched Segments to Determine Linkage of Dataset in a Database," published on Feb. 4, 2021. For example, the computing server 130 may receive a target individual genotype dataset and a plurality of additional individual genotype datasets that include haplotypes of additional individuals. For example, the additional individuals may be reference panels or individuals who are linked (e.g., in a family tree) to the target individual. The computing server 130 may generate a plurality of sub-cluster pairs of first parental groups and second parental groups. Each sub-cluster pair may be in a window. The window may correspond to a genomic segment and has a similar concept of window used in the ethnicity estimation engine 245 and the rest of the disclosure related to HMMs, but how windows are precisely divided and defined may be the same or different in the phasing engine 220 and in an HMM. Each sub-cluster pair may correspond to a genetic locus. In some embodiments, each sub-cluster pair may have a first parental group that includes a first set of matched haplotype segments selected from the plurality of additional individual datasets and a second parental group that includes a second set of matched haplotype segments selected from the plurality of additional individual datasets. The computing server 130 may generate a super-cluster of a parental side by linking the first parental groups and the second parental groups across a plurality of genetic loci (across a plurality of sub-cluster pairs). Generating the super-cluster of the parental side may include generating a candidate parental side assignment of parental groups across a set of sub-cluster pairs that represent a set of genetic loci in the plurality of genetic loci. The computing server 130 may determine the number of common additional individual genotype datasets that are classified in the candidate parental side assignment. The computing server 130 may determine the candidate parental side assignment to be part of the super-cluster based on the number of common additional individual genotype datasets. Any suitable algorithms may be used to generate the super-cluster, such as a heuristic scoring approach, a bipartite graph approach, or another suitable approach. The computing server 130 may generate a haplotype phasing of the target individual from the super-cluster of the parental side.

The IBD estimation engine 225 estimates the amount of shared genetic segments between a pair of individuals based on phased genotype data (e.g., haplotype datasets) that are stored in the genetic data store 205. IBD segments may be segments identified in a pair of individuals that are putatively determined to be inherited from a common ancestor. The IBD estimation engine 225 retrieves a pair of haplotype datasets for each individual. The IBD estimation engine 225 may divide each haplotype dataset sequence into a plurality of windows. Each window may include a fixed number of SNP sites (e.g., about 100 SNP sites). The IBD estimation engine 225 identifies one or more seed windows in which the alleles at all SNP sites in at least one of the phased haplotypes between two individuals are identical. The IBD estimation engine 225 may expand the match from the seed windows to nearby windows until the matched windows reach the end of a chromosome or until a homozygous mismatch is found, which indicates the mismatch is not attributable to potential errors in phasing or imputation. The IBD estimation engine 225 determines the total length of matched segments, which may also be referred to as IBD segments. The length may be measured in the genetic distance in the unit of centimorgans (cM). A unit of centimorgan may be a genetic length. For example, two genomic positions that are one cM apart may have a 1% chance during each meiosis of experiencing a recombination event between the two positions. The computing server 130 may save data regarding individual pairs who share a length of IBD segments exceeding a predetermined threshold (e.g., 6 cM), in a suitable data store such as in the genealogy data store 200. U.S. Pat. No. 10,114,922, entitled "Identifying Ancestral Relationships Using a Continuous stream of Input," granted on Oct. 30, 2018, and U.S. Pat. No. 10,720,229, entitled "Reducing Error in Predicted Genetic Relationships," granted on Jul. 21, 2020, describe example embodiments of IBD estimation.

Typically, individuals who are closely related share a relatively large number of IBD segments, and the IBD segments tend to have longer lengths (individually or in aggregate across one or more chromosomes). In contrast, individuals who are more distantly related share relatively fewer IBD segments, and these segments tend to be shorter (individually or in aggregate across one or more chromosomes). For example, while close family members often share upwards of 71 cM of IBD (e.g., third cousins), more distantly related individuals may share less than 12 cM of IBD. The extent of relatedness in terms of IBD segments between two individuals may be referred to as IBD affinity. For example, the IBD affinity may be measured in terms of the length of IBD segments shared between two individuals.

Community assignment engine 230 assigns individuals to one or more genetic communities based on the genetic data of the individuals. A genetic community may correspond to an ethnic origin or a group of people descended from a common ancestor. The granularity of genetic community classification may vary depending on embodiments and methods used to assign communities. For example, in some embodiments, the communities may be African, Asian, European, etc. In another embodiment, the European community may be divided into Irish, German, Swedes, etc. In yet another embodiment, the Irish may be further divided into Irish in Ireland, Irish who immigrated to America in 1800, Irish who immigrated to America in 1900, etc. The community classification may also depend on whether a population is admixed or unadmixed. For an admixed population, the classification may further be divided based on different ethnic origins in a geographical region.

Community assignment engine 230 may assign individuals to one or more genetic communities based on their inheritance datasets using machine learning models trained by unsupervised learning or supervised learning. In an unsupervised approach, the community assignment engine 230 may generate data representing a partially connected undirected graph. In this approach, the community assignment engine 230 represents individuals as nodes. Some nodes are connected by edges whose weights are based on IBD affinity between two individuals represented by the nodes. For example, if the total length of two individuals' shared IBD segments does not exceed a predetermined threshold, the nodes are not connected. The edges connecting two nodes are associated with weights that are measured based on the IBD affinities. The undirected graph may be referred to as an IBD network. The community assignment engine 230 uses clustering techniques such as modularity measurement (e.g., the Louvain method) to classify nodes into different clusters in the IBD network. Each cluster may represent a community. The community assignment engine 230 may also determine sub-clusters, which represent sub-communities. The computing server 130 saves the data representing the IBD network and clusters in the IBD network data store 235. U.S. Pat. No. 10,223,498, entitled "Discovering Population Structure from Patterns of Identity-By-Descent," granted on Mar. 5, 2019, describes example embodiments of community detection and assignment.

The community assignment engine 230 may also assign communities using supervised techniques. For example, inheritance datasets of known genetic communities (e.g., individuals with confirmed ethnic origins) may be used as training sets that have labels of the genetic communities. Supervised machine learning classifiers, such as logistic regressions, support vector machines, random forest classifiers, and neural networks may be trained using the training set with labels. A trained classifier may distinguish binary or multiple classes. For example, a binary classifier may be trained for each community of interest to determine whether a target individual's inheritance dataset belongs or does not belong to the community of interest. A multi-class classifier such as a neural network may also be trained to determine whether the target individual's inheritance dataset most likely belongs to one of several possible genetic communities.

Reference panel sample store 240 stores reference panel samples for different genetic communities. A reference panel sample is the genetic data of an individual whose genetic data is the most representative of a genetic community. The genetic data of individuals with the typical alleles of a genetic community may serve as reference panel samples. For example, some alleles of genes may be over-represented (e.g., being highly common) in a genetic community. Some inheritance datasets include alleles that are commonly present among members of the community. Reference panel samples may be used to train various machine learning models in classifying whether a target inheritance dataset belongs to a community, determining the ethnic composition of an individual, and determining the accuracy of any genetic data analysis, such as by computing a posterior probability of a classification result from a classifier.

A reference panel sample may be identified in different ways. In some embodiments, an unsupervised approach in community detection may apply the clustering algorithm recursively for each identified cluster until the sub-clusters contain a number of nodes that are smaller than a threshold (e.g., containing fewer than 1000 nodes). For example, the community assignment engine 230 may construct a full IBD network that includes a set of individuals represented by nodes and generate communities using clustering techniques. The community assignment engine 230 may randomly sample a subset of nodes to generate a sampled IBD network. The community assignment engine 230 may recursively apply clustering techniques to generate communities in the sampled IBD network. The sampling and clustering may be repeated for different randomly generated IBD networks for various runs. Nodes that are consistently assigned to the same genetic community when sampled in various runs may be classified as a reference panel sample. The community assignment engine 230 may measure the consistency in terms of a predetermined threshold. For example, if a node is classified to the same community 95% (or another suitable threshold) of the times the node is sampled, the inheritance dataset corresponding to the individual represented by the node may be regarded as a reference panel sample. Additionally, or alternatively, the community assignment engine 230 may select N most consistently assigned nodes as a reference panel for the community.

Other ways to generate reference panel samples are also possible. For example, the computing server 130 may collect a set of samples and gradually filter and refine the samples until high-quality reference panel samples are selected. For example, a candidate reference panel sample may be selected from an individual whose recent ancestors were born at a certain birthplace. The computing server 130 may also draw sequence data from the Human Genome Diversity Project (HGDP). Various candidates may be manually screened based on their family trees, relatives' birth location, and other quality controls. Principal component analysis may be used to create clusters of genetic data of the candidates. Each cluster may represent an ethnicity. The predictions of the ethnicity of those candidates may be compared to the ethnicity information provided by the candidates to perform further screening.

The ethnicity estimation engine 245 estimates the ethnicity composition of an inheritance dataset of a target individual. The inheritance datasets used by the ethnicity estimation engine 245 may be genotype datasets or haplotype datasets. For example, the ethnicity estimation engine 245 estimates the ancestral origins (e.g., ethnicity) based on the individual's genotypes or haplotypes at the SNP sites. To take a simple example of three ancestral populations corresponding to African, European and Native American, an admixed user may have nonzero estimated ethnicity proportions for all three ancestral populations, with an estimate such as [0.05, 0.65, 0.30], indicating that the user's genome is 5% attributable to African ancestry, 65% attributable to European ancestry and 30% attributable to Native American ancestry. The ethnicity estimation engine 245 generates the ethnic composition estimate and stores the estimated ethnicities in a data store of computing server 130 with a pointer in association with a particular user.

In some embodiments, the ethnicity estimation engine 245 divides a target inheritance dataset into a plurality of windows (e.g., about 1000 windows). Each window includes a small number of SNPs (e.g., 300 SNPs). The ethnicity estimation engine 245 may use a directed acyclic graph model to determine the ethnic composition of the target inheritance dataset. The directed acyclic graph may represent a trellis of an inter-window hidden Markov model (HMM). The graph includes a sequence of a plurality of node groups. Each node group, representing a window, includes a plurality of nodes. The nodes represent different possibilities of labels of genetic communities (e.g., ethnicities) for the window. A node may be labeled with one or more ethnic labels. For example, a level includes a first node with a first label representing the likelihood that the window of SNP sites belongs to a first ethnicity and a second node with a second label representing the likelihood that the window of SNPs belongs to a second ethnicity. Each level includes multiple nodes so that there are many possible paths to traverse the directed acyclic graph.

The nodes and edges in the directed acyclic graph may be associated with different emission probabilities and transition probabilities. An emission probability associated with a node represents the likelihood that the window belongs to the ethnicity labeling the node given the observation of SNPs in the window. The ethnicity estimation engine 245 determines the emission probabilities by comparing SNPs in the window corresponding to the target inheritance dataset to corresponding SNPs in the windows in various reference panel samples of different genetic communities stored in the reference panel sample store 240. The transition probability between two nodes represents the likelihood of transition from one node to another across two levels. The ethnicity estimation engine 245 determines a statistically likely path, such as the most probable path or a probable path that is at least more likely than 95% of other possible paths, based on the transition probabilities and the emission probabilities. A suitable dynamic programming algorithm such as the Viterbi algorithm or the forward-backward algorithm may be used to determine the path. After the path is determined, the ethnicity estimation engine 245 determines the ethnic composition of the target inheritance dataset by determining the label compositions of the nodes that are included in the determined path. U.S. Pat. No. 10,558,930, entitled "Local Genetic Ethnicity Determination System," granted on Feb. 11, 2020, and U.S. Pat. No. 10,692,587, granted on Jun. 23, 2020, entitled "Global Ancestry Determination System" describe different example embodiments of ethnicity estimation.

The tree management engine 250 performs computations and other processes related to users' management of their data trees such as family trees. The tree management engine 250 may allow a user to build a data tree from scratch or to link the user to existing data trees. In some embodiments, the tree management engine 250 may suggest a connection between a target individual and a family tree that exists in the family tree database by identifying potential family trees for the target individual and identifying one or more most probable positions in a potential family tree. A user (target individual) may wish to identify family trees to which he or she may potentially belong. Linking a user to a family tree or building a family may be performed automatically, manually, or using techniques with a combination of both. In an embodiment of an automatic tree matching, the tree management engine 250 may receive an inheritance dataset from the target individual as input and search related individuals that are IBD-related to the target individual. The tree management engine 250 may identify common ancestors. Each common ancestor may be common to the target individual and one of the related individuals. The tree management engine 250 may in turn output potential family trees to which the target individual may belong by retrieving family trees that include a common ancestor and an individual who is IBD-related to the target individual. The tree management engine 250 may further identify one or more probable positions in one of the potential family trees based on information associated with matched genetic data between the target individual and those in the potential family trees through one or more machine learning models or other heuristic algorithms. For example, the tree management engine 250 may try putting the target individual in various possible locations in the family tree and determine the highest probability position(s) based on the inheritance dataset of the target individual and inheritance datasets available for others in the family tree and based on genealogy data available to the tree management engine 250. The tree management engine 250 may provide one or more family trees from which the target individual may select. For a suggested family tree, the tree management engine 250 may also provide information on how the target individual is related to other individuals in the tree. In a manual tree building, a user may browse through public family trees and public individual entries in the genealogy data store 200 and individual profile store 210 to look for potential relatives that can be added to the user's family tree. The tree management engine 250 may automatically search, rank, and suggest individuals for the user conduct manual reviews as the user makes progress in the front-end interface 260 in building the family tree.

As used herein, "pedigree" and "family tree" may be interchangeable and may refer to a family tree chart or pedigree chart that shows, diagrammatically, family information, such as family history information, including parentage, offspring, spouses, siblings, or otherwise for any suitable number of generations and/or people, and/or data pertaining to persons represented in the chart. U.S. Pat. No. 11,429,615, entitled "Linking Individual Datasets to a Database," granted on Aug. 30, 2022, describes example embodiments of how an individual may be linked to existing family trees.

The front-end interface 260 may render a front-end platform that displays various results determined by the computing server 130. The platform may take the form of a genealogy research and family tree building platform and/or a personal DNA data analysis platform. The platform may also serve as a social networking system that allows users and connect and build family trees and research family relations together. The results and data may include the IBD affinity between a user and another individual, the community assignment of the user, the ethnicity estimation of the user, phenotype prediction and evaluation, genealogy data search, family tree and pedigree, relative profile and other information. The front-end interface 260 may allow users to manage their profile and data trees (e.g., family trees). The users may view various public family trees stored in the computing server 130 and search for individuals and their genealogy data via the front-end interface 260. The computing server 130 may suggest or allow the user to manually review and select potentially related individuals (e.g., relatives, ancestors, close family members) to add to the user's data tree. The front-end interface 260 may be a graphical user interface (GUI) that displays various information and graphical elements.

The front-end interface 260 may take different forms. In one case, the front-end interface 260 may be a software application that can be displayed on an electronic device such as a computer or a smartphone. The software application may be developed by the entity controlling the computing server 130 and be downloaded and installed on the client device 110. In another case, the front-end interface 260 may take the form of a webpage interface of the computing server 130 that allows users to access their family tree and genetic analysis results through web browsers. In yet another case, the front-end interface 260 may provide an application program interface (API). In some embodiments, the front-end interface 260 may be rendered as part of the content in an extended reality device, such as a head-mounted display or a phone camera that is integrated with augmented reality features.

The front-end interface 260 may provide various front-end visualization features. In some embodiments, a family tree viewer may render family tree built by users and/or managed by the tree management engine 250. The family tree may be displayed in a nested nodes and edges connected based on family relationships or genetic matches determined by various genetic data analysis engines discussed in FIG. 2. The family trees may include attached records that are part of records in the genealogy data store 200, including records that are uploaded by users and gallery images. The user may assign a focal person to a family tree and the family tree is displayed with the focus (such as positioning the focal person at the center or relative prominent position of the tree) around the focal person. A user may change the focal person and the family tree may shift accordingly based on the relationships and relative positions of members in the family tree. Each person in the family tree may be associated with historical photos from gallery images, historical genealogy records such as life event records, one or more stories and live events associated with the person, and metadata such as family relationships and other family trees associated with the person.

In some embodiments, visualization features provided by the front-end interface 260 may include a map feature. A map may be a geographical map that may take the form of a digital map, a historical physical map, and/or a historical map overlaid on a digital map. A user may select a geographical location and the front-end interface 260 displays relevant genealogical or genetic records associated with the location, such as an ancestor's lifetime events, birth locations of DNA matches, mitigation patterns of ancestors across different locations over time and associated genealogical records, residence maps that provide specific locations of historical persons' events, and historical maps overlaying on a digital map to contextualize ancestors' records and events. The map feature may also provide interactive features to allow users to view historical documents, photographs, and stores associated with the geographical locations. The map feature may also allow users to adjust timeframes, displaying changes in locations and migrations over different periods.

In some embodiments, visualization features provided by the front-end interface 260 may include a story feature that provides multimedia narratives about a person, such as the person's live events and family history. The story feature allows a user to compile various graphical and genealogical elements such as photos, documents, historical records, and personal anecdotes into a timeline to summarize a narrative. The story may be arranged in an appropriate spatial manner such as a linear arrangement that arranges various graphical elements based on the creator's selection.

In this disclosure, a genetic data may be an example of inheritance data. An individual is an example of a named entity. A genetic sequence is an example of data string or bit string. A genetic segment is an example of data string segment. A matched genetic segment is an example of matched data string. For example, an IBD segment is an example of a matched data string segment. An ethnicity is an example or a data origin or a data classification. A phenotype, or a phenotypic trait, is an example of a data manifestation, and both "phenotype" and "phenotypic trait" are used interchangeably herein. A reproductive event is an example of a data inheritance event.

The phenotype prediction engine 265 predicts whether a target individual has a phenotypic trait using a polygenic risk score (PRS) calculated from genetic datasets of the target individual. A phenotypic trait is an observable physical trait of human individuals. Phenotypic traits are examples of data manifestations because they are manifestation as observable traits from the underlying genetic data. While phenotypic traits are used as examples in this present application, the association studies and other related prediction analyses may also be used to predict other data manifestations that might or might not be related to the phenotypes or genetics of an individuals, such as traits like environmental factors, preferences, experiences, and other suitable identifiable traits that may be obtained from survey responses or other data.

The genetic datasets used may be genotype datasets or haplotype datasets and are examples of inheritance datasets. The phenotype prediction engine 265 identifies a subset of SNP loci from the plurality of SNP loci genotyped from a DNA sample of the target individual, with each SNP locus in the subset of SNP loci selected based on predictive ability of the phenotypic trait or other information. The phenotype prediction engine 265 calculates a PRS for the target individual based on genotypes at or genotyping data of the subset of SNP loci. The PRS is compared against one or more PRS thresholds for positively predicting that the target individual has the phenotypic trait. The prediction of the phenotypic trait using the PRS will be described further in FIGS. 3-4. The PRS is an example of an association score, which may also be referred to as an aggregated data-bit association score because the PRS is aggregated from various SNP locations (data bits in the genetic data).

The PRS threshold may be identified using a plurality of training samples associated with other individuals, whom may be referred to as training individuals. Among the plurality of training individuals, some are reported to have the phenotypic trait and others are reported to not have the phenotypic trait. The reports of the phenotypic trait may be obtained from any suitable sources. For example, the reports may be obtained from the survey responses stored in a database, from consented medical history or records of the training individuals, from input data of the training individuals provided to or accessed by the computing server 130, etc. The phenotype prediction engine 265 calculates a PRS for each training individual based on each individual's genotypes at or genotyping data of the subset of SNP loci. Sweeping through the domain of PRS, i.e., a range of candidate PRS thresholds, for the subset of SNP loci, the phenotype prediction engine 265 can calculate a receiver operating characteristic (ROC) curve plotting a true positive rate to a false positive rate for predicting the phenotypic trait among the training individuals. The true positive rate may correspond to a percentage of training individuals reported to have the phenotypic trait that were accurately predicted to have the phenotypic trait. The false positive rate may correspond to a percentage of training individuals reported to not have the phenotypic trait that were inaccurately predicted to have the phenotypic trait. The phenotype prediction engine 265 selects one of the candidate PRS thresholds as the PRS threshold based on the true positive rate and the false positive rate corresponding to the selected one of the candidate PRS thresholds. The selected candidate PRS threshold may be selected to ensure a sufficiently high true positive rate and a sufficiently low false positive rate, i.e., an optimal PRS threshold that maximizes the true rate and minimizes the false positive rate. For example, ratios of the true positive rate to the false rate may be determined over different candidate PRS thresholds. A PRS threshold corresponding to the highest value of the ratio may be selected. Other suitable ways may also be used to select the PRS threshold.

Phenotype Prediction with Polygenic Risk Scoring

Figure 3:
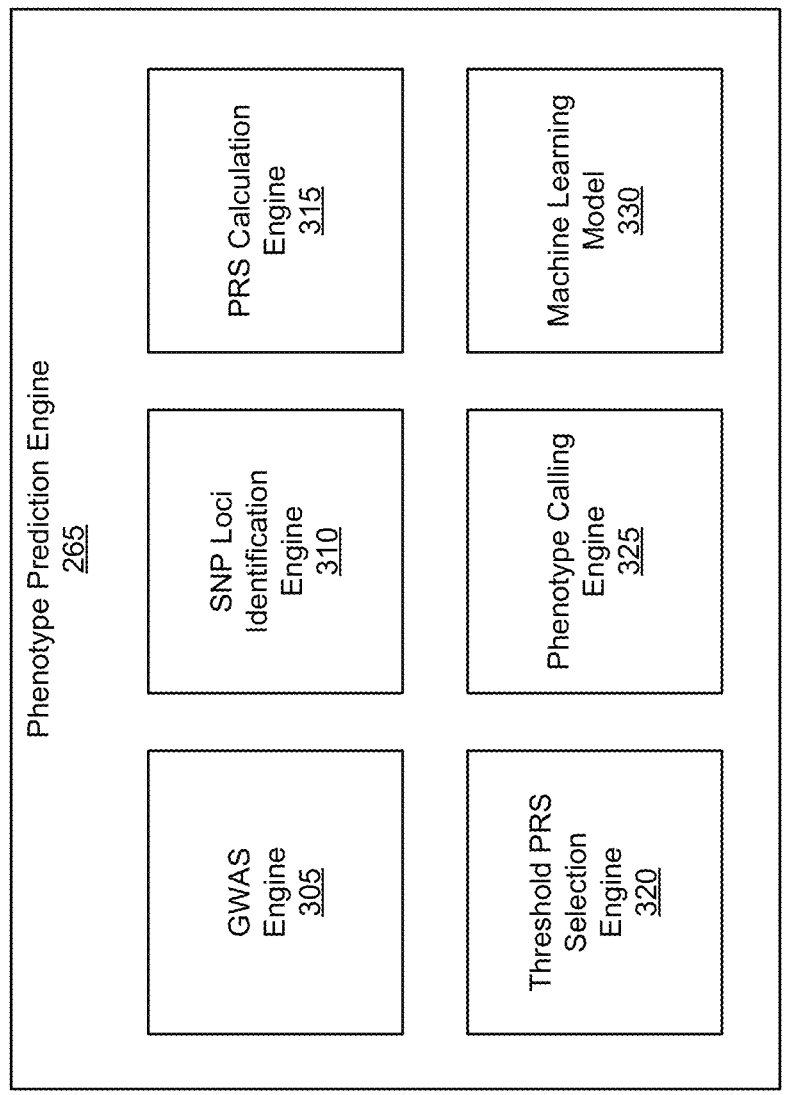
FIG. 3 is a block diagram of an architecture of an example phenotype prediction engine 265, in accordance with some embodiments.

FIG. 3 is a block diagram of an architecture of an example phenotype prediction engine 265, in accordance with an embodiment. The phenotype prediction engine 265 predicts whether an individual, such as a target individual, has a particular phenotypic trait based on the individual's inheritance dataset. The phenotype prediction engine 265 has a genome-wide association study (GWAS) engine 305, a SNP loci identification engine 310, a PRS calculation engine 315, a PRS threshold selection engine 320, and a phenotype calling engine 325. Alternatively, or additionally, the phenotype prediction engine 265 uses a machine learning model 330 for predicting the phenotypic trait. In various embodiments, the phenotype prediction engine 265 includes additional or fewer components than those listed herein. The phenotype prediction engine 265 may also include different components. Moreover, functions described under the engines may be variably distributed according to other implementations of the principles described herein.

In conducting a GWAS, the GWAS engine 305 obtains a plurality of inheritance datasets associated with training individuals. The plurality of training individuals may be narrowed according to an ethnicity prediction, e.g., the training individuals are all from a particular geographical origin or associated with a particular ethnicity origin. In another embodiment, the training individuals are rather (or additionally) narrowed by genetic community, providing a more-granular and/or more-recent scale than ethnicity. The determination of ethnicity and/or genetic community may be performed using the community assignment engine 230 and/or the ethnicity estimation engine 245. The training individuals include at least a first subset of positive training individuals, i.e., training individuals reported to have the phenotypic trait in consideration, and a second subset of negative training individuals, i.e., training individuals reported to not have the phenotypic trait. Each training individual has an inheritance dataset comprising genotypes or genotyping data over or for a plurality of SNP loci genotyped, e.g., by the computing server 130. Reporting by an individual on whether or not that individual has a phenotypic trait may be collected in surveys and stored, e.g., in the individual profile store 210.

The GWAS engine 305 conducts a GWAS for a phenotypic trait with the plurality of training individuals. In conducting the GWAS, the GWAS engine 305, at each SNP locus genotyped or otherwise identified in the genetic datasets of the training individuals, counts a first percentage of positive training individuals with a genotype including the SNP and counts a second percentage of negative training individuals with a genotype including the SNP. The GWAS engine 305 can calculate a predictive score for each SNP locus according to the first percentage and the second percentage, e.g., an odds ratio of the first percentage to the second percentage. In some embodiments, the GWAS engine 305 calculates a p-value score as the predictive score, wherein the p-value score indicates a likelihood of observing a result that is equal to or more extreme, e.g. greater than, than the actual observed percentages. The GWAS engine 305 may tabulate the predictive scores (e.g., p-value scores) for each SNP locus. That is, the p-value determined for one or more SNP loci may indicate the statistical significance of the associated SNP loci on an individual's likelihood of exhibiting the trait. For a plurality of SNPs associated through GWAS with a particular trait, p-values and associated beta values (which may be a model coefficient, such as logistic for binary traits) may be determined as shown in Table 1 below.

TABLE 1

| SNP ID | p-value | Effect Allele | Beta |
|---|---|---|---|
| SNP1 (A/G) | <0.001 | A | −0.01 |
| SNP2 (C/T) | <0.001 | T | 0.05 |
| SNP3 (A/C) | <0.001 | A | 0.06 |
| SNP4 (G/T) | <0.001 | T | 0.12 |
| SNP5 (A/C) | <0.001 | A | −0.03 |
| SNP6 (G/A) | 0.8 | T | 0.001 |

In some embodiments, the phenotypic trait comprises a plurality of labels, e.g., various eye colors. In these embodiments, the GWAS engine 305 may conduct the GWAS by considering each label against the remaining labels. For example, when considering a first label, each training individual of that first label (e.g. having that particular trait) would be considered a positive training individual while the remaining training individuals would be considered a negative training individual. The GWAS engine 305 may then apply a similar principle described above to calculate a predictive score for each SNP locus according to or based on percentages of the positive training individuals and the negative training individuals. The GWAS engine 305 may iterate through each of the labels calculating a predictive score for each SNP locus indicating predictive ability of each label. The predictive scores for a given SNP locus may be aggregated in some manner, e.g., average, median, maximum, minimum, etc.

Referring back to FIG. 3, the SNP loci identification engine 310 selects SNP loci for consideration in determining a PRS. The SNP loci identification engine 310 obtains the predictive scores (e.g., p-value scores) for each SNP locus genotyped by the computing server 130 for individuals. The SNP loci identification engine 310 identifies a subset of the SNP loci with or using a predictive score threshold. Considering the example with the predictive score calculated as a p-value score, the SNP loci identification engine 310 identifies the subset of SNP loci by including SNP loci with a p-value score below the p-value threshold, e.g., 0.05, 0.01, 1E-5, etc. In some embodiments, the SNP loci identification engine 310 further filters SNP loci that have some degree of linkage disequilibrium with other SNP loci. Linkage disequilibrium (LD) refers to the non-random association between alleles at different loci in the human population. To measure a degree of LD between two SNPs at two SNP loci, a difference is calculated between a product of the likelihoods of observing the SNPs independently and the likelihood of observing the SNPs together. The SNP loci identification engine 310 may set a threshold for filtering SNPs with a degree of LD above a threshold. The threshold may be set for greedy or non-greedy inclusion of SNP loci in the subset of SNP loci.

The PRS calculation engine 315 calculates a PRS for an individual vis-à-vis the trait according to the individual's genotypes for the identified subset of SNP loci. The PRS calculation engine 315 maintains a PRS function that inputs the genotypes or genotyping data over the identified subset of SNP loci and outputs a PRS. In some implementations, the PRS function is a linear function with a weight for each SNP locus in the identified subset. Genotypes or genotyping data of the SNP locus may be binary values (e.g., whether or not the individual has the dominant allele) or trinary values (e.g., homozygous with the first allele, heterozygous, homozygous with the second allele). The weights may be determined based on predictive scores from or determined by the GWAS engine 305. The PRS function may further normalize the PRS, e.g., limiting the domain of the PRS in the range of [0, 1]. In other embodiments, the PRS calculation engine 315 may employ other techniques in calculating the PRS, e.g., Bayesian approaches considering linkage disequilibrium prediction, penalized regression techniques, etc.

For example, the PRS may be determined using weights or other factors as shown in Table 2 below, with, in embodiments, the PRS being a sum of weighted betas.

TABLE 2

| SNP ID | p-value | Effect Allele | Beta | Beta*X |
| --- | --- | --- | --- | --- |
| SNP1 (A/G) | <0.001 | A | −0.01 | −0.01 |
| SNP2 (C/T) | <0.001 | T | 0.05 | 2*0.05 |
| SNP3 (A/C) | <0.001 | A | 0.06 | 0 |
| SNP4 (G/T) | <0.001 | T | 0.12 | 0.12 |
| SNP5 (A/C) | <0.001 | A | −0.03 | −0.03 |
| SNP6 (G/A) | 0.8 | T | 0.001 | −0.01 |
|  |  |  | PRS | 1.08 |

The PRS threshold selection engine 320 selects a PRS threshold for predicting the phenotypic trait. The PRS threshold selection engine 320 utilizes a plurality of training individuals (which can be the same plurality used to conduct the GWAS by the GWAS engine 305). The training individuals are collected according to similar principles as described above in the GWAS engine 305. The PRS threshold selection engine 320 obtains a PRS for each of the training individuals calculated by the PRS calculation engine 315 according to an identified subset of SNP loci with or meeting a predictive score threshold (e.g., SNP loci with p-value scores under 0.05). The PRS threshold selection engine 320 sweeps a domain of the PRS for the identified subset, i.e., a range of candidate PRS thresholds (e.g., the domain range from [0, 1]), to test candidate PRS thresholds and predict a number of the training individuals with PRSs above the candidate PRS threshold to have the phenotypic trait. The PRS threshold calculation engine 320 can calculate a true positive rate as a percentage of positive training individuals (training individuals reported to have the phenotypic trait) that were accurately predicted to have the phenotypic trait. The PRS threshold calculation engine 320 can also calculate a false positive rate as a percentage of negative training individuals (training individuals reported to not have the phenotypic trait) that were inaccurately predicted to have the phenotypic trait. The PRS threshold calculation engine 320 may perform additional statistical calculations on the prediction, e.g., true negative, false negative, precision, recall, etc.

According to one or more embodiments, the PRS threshold selection engine 320 selects one of the candidate PRS thresholds over the range of candidate PRS thresholds as the PRS threshold based on at least the true positive rate and the false positive rate corresponding to the selected candidate PRS threshold. The selected candidate PRS threshold may be selected so as to achieve a sufficiently high true positive rate and a sufficiently low false positive rate. In an ideal case, a perfect PRS threshold has a true positive rate in predicting positive training individuals of 100% and a false positive rate of 0%. Thus, the PRS threshold that has a sufficiently high true positive rate and a sufficiently low false positive rate may be closest to the perfect PRS threshold. In other embodiments, the PRS threshold is selected based on other statistics calculated (e.g., true negative, false negative etc.) in substitution of or in addition to the true positive and false positive rates.

In embodiments with multiple labels, the PRS threshold selection engine 320 may select a PRS threshold for each label of the phenotypic trait to stratify the prediction. For each label, the PRS threshold selection engine 320 may (similarly with the binary label) sweep through the domain of the PRS to test PRS thresholds to generate a ROC curve plotting true positive rate against false positive rate, wherein the training individuals of the label being considered (i.e. those reported to have the phenotypic trait) would be considered positive training individuals while remaining training individuals would be considered negative training individuals. The PRS selection engine 320 may select the optimal PRS threshold from the ROC curve as the PRS threshold for that label. Upon selecting a PRS threshold for each label of the plurality of labels for the phenotypic trait, the domain of the PRS may be stratified with the PRS thresholds such that a range of PRSs would yield a prediction for each label. In an example with three labels, the PRS threshold selection engine 320 chooses a PRS threshold of 0.2 for the first label, a PRS threshold of 0.6 for the second label, and a PRS threshold of 0.8 for the third label, such that a PRS within [0, 0.2) calls a null label (e.g., none of the three labels), a PRS within [0.2, 0.6) calls the first label, a PRS within [0.6, 0.8) calls the second label, and a PRS within [0.8, 1.0] calls the third label.

Figure 4:
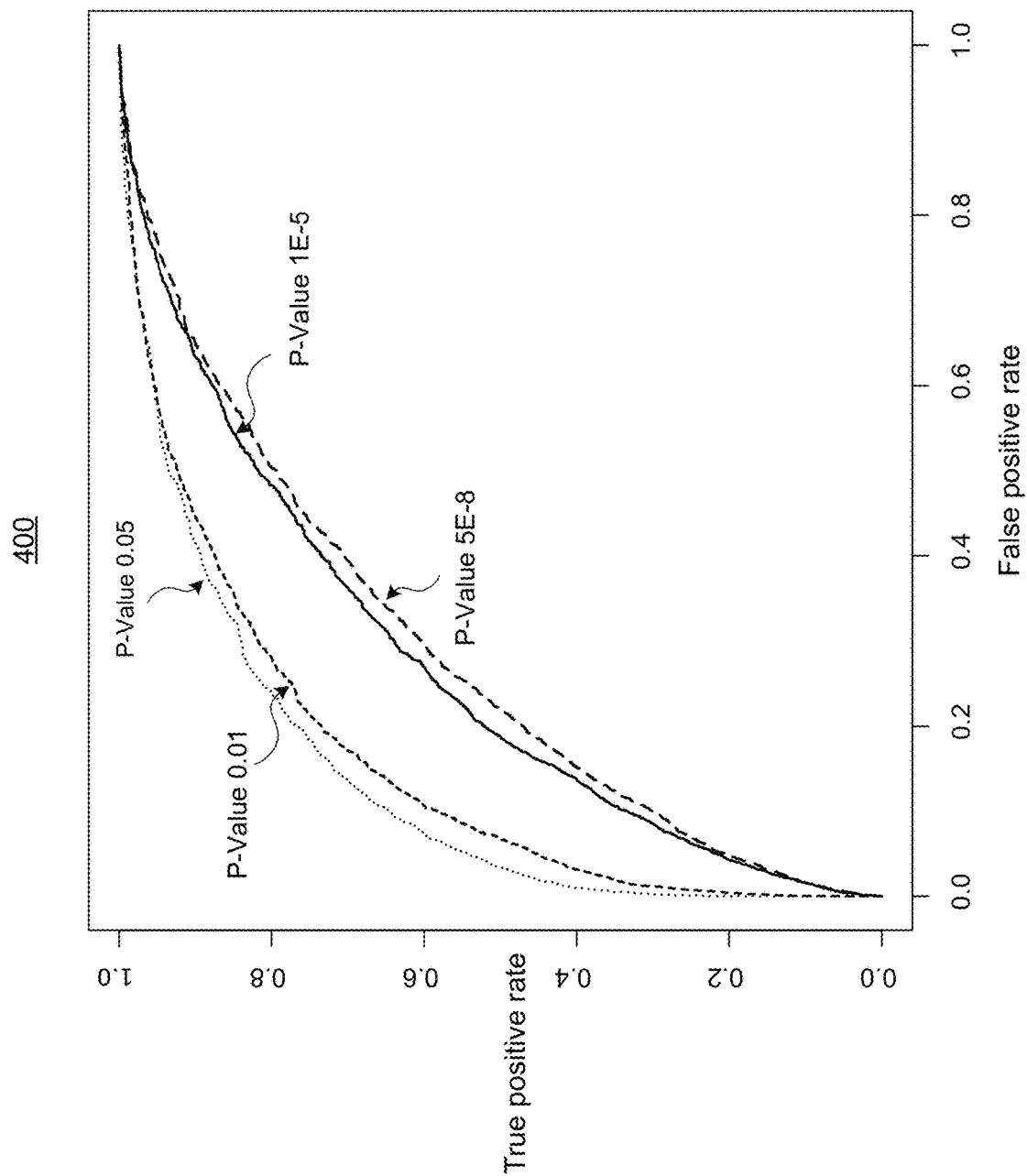
FIG. 4 illustrates a graph of predictive sensitivity over a domain of polygenic risk score for four different subsets of SNP loci, in accordance with some embodiments.

Referring to FIG. 4, there is shown a graph 400 of predictive sensitivity over a domain or range of PRSs for four different subsets of SNP loci, in accordance with an embodiment. The four different subsets of SNP loci correspond to different p-value score cutoffs. A first subset with a p-value cutoff of 0.05 includes roughly 30,000 SNP loci used for calculating the PRS. A second subset with a p-value cutoff of 0.01 includes roughly 8,000 SNP loci. A third subset with a p-value cutoff of 1E-5 includes roughly 400 SNP loci. A fourth subset with a p-value cutoff of 5E-8 includes roughly 200 SNP loci. For each subset of SNP loci, the PRS threshold calculation engine 320 sweeps through the domain of PRS and calculates a true positive rate and a false positive rate.

The graph 400 plots receiver operating characteristic (ROC) curves for the four subsets over the domain of PRS. The ideal PRS threshold is at (1, 0) where the true positive rate is 100% and the false positive rate is 0%. The PRS threshold can be identified from each subset as the closest (e.g., by Euclidean distance) to the point (1, 0), i.e., sufficiently high true positive rate and sufficiently low false positive rate. For example, with the ROC curve for the p-value of 0.05, the closest point to the ideal PRS threshold is roughly (0.77, 0.21), e.g., which might correspond to a PRS threshold of 0.4. The PRS threshold selection engine 320 can identify that PRS of 0.4 as the PRS threshold for use in predicting the phenotypic trait.

In some embodiments, the SNP loci identification engine 310 determines a p-value threshold that optimizes overall predictability of the subset of SNP loci. As shown in the graph 400, each subset's ROC curve is unique with varying degrees of overall predictability. ROC curves that tend towards the ideal PRS threshold have better overall predictability. As shown in the graph 400, the subsets can be ordered according to overall predictability, with the following order: the first subset, the second subset, the third subset, and the fourth subset, given that the first subset has higher true-positive/false-positive rates/ratios. The overall predictability may be based on the closest PRS on the ROC curve to the ideal PRS threshold or some holistic measure, which ROC curve is greater over a majority of the false positive domain.

The phenotype calling engine 325 predicts whether an individual has a phenotypic trait according to the individual's PRS. The phenotype calling engine 325 obtains a PRS for an individual calculated by the PRS calculation engine 315 according to an identified subset of SNP loci (e.g., selected with a p-value cutoff of 0.05). The phenotype calling engine 325 further obtains the PRS threshold (or in cases with multiple labels for phenotypic trait, the PRS thresholds) for predicting whether an individual has the particular phenotypic trait from the PRS threshold selection engine 320. The phenotype calling engine 325 compares the individual's PRS to the PRS threshold(s) and predicts whether the individual likely has the phenotypic trait based on the comparison (or predicts one of the labels of the phenotypic trait in pluralistic phenotypic traits). As a numerical example, the individual's PRS may be 0.5 which, when compared against the PRS threshold of 0.4, results in a prediction that the individual has the phenotypic trait. The phenotype calling engine 325 may provide the prediction—"likely has" or "likely does not have" the phenotypic trait—to the front-end interface 260, e.g., for presentation to the individual or to other users via a client device 110. In embodiments where the phenotypic trait is or is on a continuum, the phenotype calling engine 325 may retrieve a trained regression modality that regresses the phenotypic trait against the PRS. The phenotype calling engine 325 inputs the individual's PRS into the trained regression to determine a value on the continuum for the phenotypic trait.

In some embodiments, the phenotype calling engine 325 may alternatively or additionally implement a machine learning model 330 to predict the phenotypic trait. The machine learning model 330 inputs a feature vector comprising genotypes or genotyping data over an identified SNP locus of the subset of SNP loci, e.g., identified by the SNP loci identification engine 310. Some or all of the identified subset of SNP loci may also be identified via other techniques. The machine learning model 330 outputs a prediction of a likelihood the individual has the phenotype. The prediction may be a binary prediction of whether the individual has or does not have the phenotype, e.g., binary classification, or may be a percent likelihood that the individual has the phenotype. In embodiments where the phenotypic trait comprises a plurality of labels, the prediction may be a multiclass prediction of which label the individual likely has or a percent likelihood that the individual has one or more of the labels in the phenotypic trait considered. For example, where the phenotypic trait considered is eye color with multiple labels such as blue, green, hazel, or brown, wherein the prediction could be the most likely eye color or a percentage likelihood or confidence associated with each eye color. In yet other embodiments, the phenotypic trait may be a continuum (e.g., height) wherein a regression is generated that outputs a prediction on the continuum. The machine learning model may be trained as the regression taking feature vectors and outputting the phenotypic trait. The phenotype prediction engine 250 may also train the machine learning model 330 with the plurality of training individuals. Different machine learning techniques may be implemented such as a support vector machine (SVM), boosting for other algorithms (e.g., AdaBoost), neural networks, logistic regression, naïve Bayes, memory-based learning, random forests, bagged trees, decision trees, boosted trees, or boosted stumps. The machine learning model may consider other features in substitution or in addition to the SNP loci. These features include but are not limited to PRS, age, sex, array sequenced on, other survey questions, phenotypes of ancestors or relatives, ethnicity, community.

Parental Influence Prediction on One or More Traits in an Individual

Figure 5:
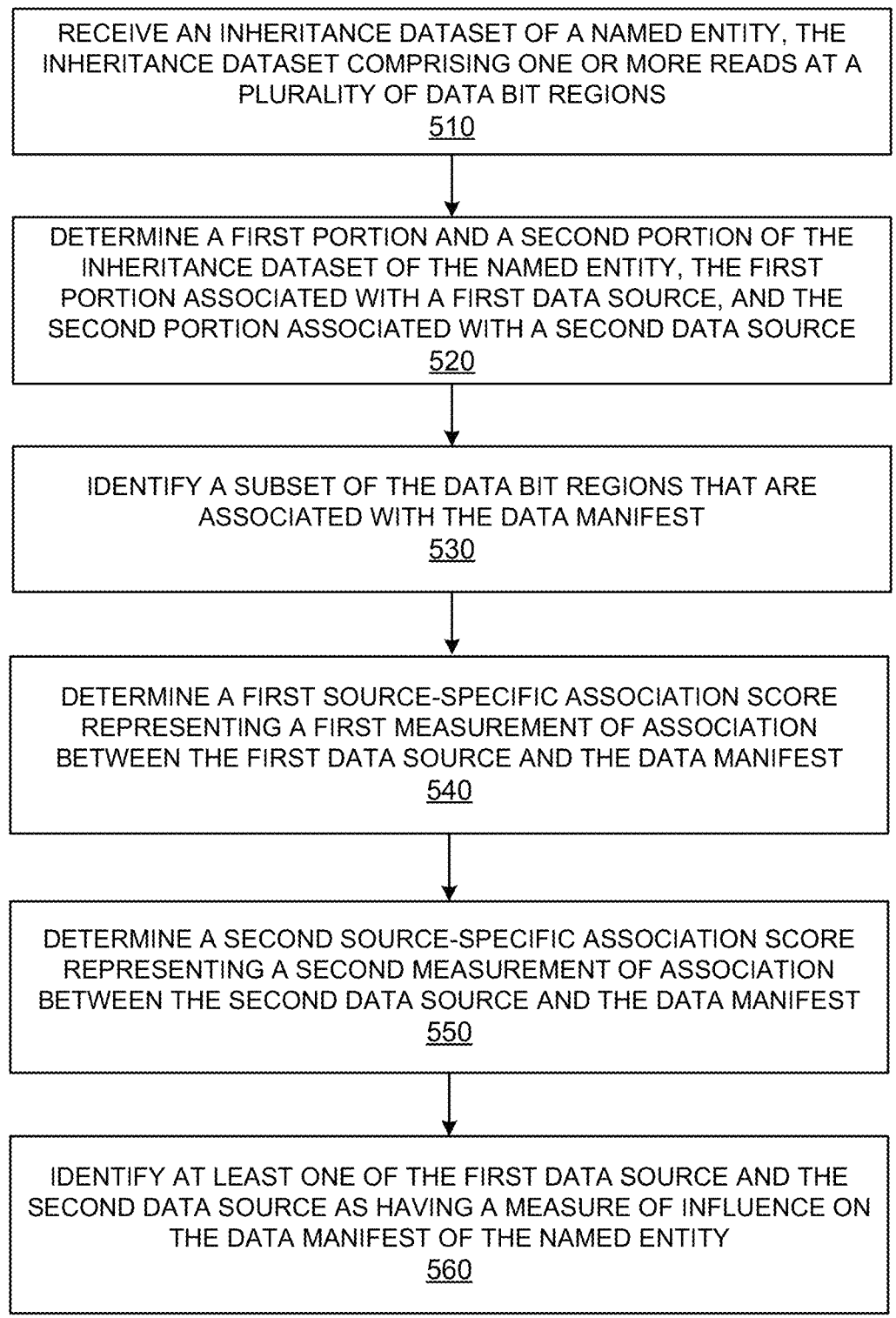
FIG. 5 is a flowchart depicting an example process for predicting parental influences on one or more traits in an individual, in accordance with some embodiments.

FIG. 5 is a flowchart depicting an example process 500 for predicting parental influences on one or more traits in an individual, in accordance with some embodiments. The process 500 may be performed by one or more engines of the computing server 130 illustrated in FIG. 2, such as the phenotype prediction engine 265. The process 500 may be embodied as a software algorithm that may be stored as computer instructions that are executable by one or more processors. The instructions, when executed by the processors, cause the processors to perform various steps in the process 500. In various embodiments, the process 500 may include additional, fewer, or different steps. While various steps in the process 500 may be discussed with the use of computing server 130, each step may be performed by a different computing device.

In this disclosure, particularly in FIG. 5 through FIG. 9, genetic data is an example of inheritance data. An individual is an example of a named entity. A genetic sequence is an example of data string or bit string. A genetic segment is an example of data string segment. A matched genetic segment is an example of a matched data string. For example, an IBD segment is an example of a matched data string segment. An ethnicity is an example of a data origin or a data classification. A parental influence is an example of a data-source influence. A first parent is an example of a first data source. A second parent (relative to a corresponding first parent) is an example of a second data source (relative to a corresponding first data source). A SNP locus is an example of a data-bit region. A first haplotype is an example of a first portion of an inheritance dataset. A second haplotype (relative to a corresponding first haplotype) is an example of a second portion (relative to a corresponding first portion) of an inheritance dataset. A PRS is an example of an aggregated data-bit association score. A trait (e.g., a phenotype) is an example of a data manifestation. A PRS determined from a haplotype of a first parent is an example of a first source-specific association score. A PRS determined from a haplotype of a second parent (relative to a corresponding first parent) is an example of a second source-specific association score.

In some embodiments, the computing server 130 can receive and/or access an inheritance dataset of a named entity, such as a target individual (step 510). The accessed inheritance dataset includes one or more reads at a plurality of SNP loci. The computing server 130 may receive the individual's inheritance dataset by interfacing with the genetic data store 205 or the individual profile store 210 of FIG. 2. For example, the computing server 130 may initiate a data request to the genetic data store 205. In response to the request, the genetic data store 205 may deliver the individual's inheritance dataset to the computing server 130.

The individual's inheritance dataset may include one or more reads at a plurality of SNP loci. As previously mentioned, the inheritance dataset of the individual may be a digital dataset of nucleotide data (e.g., genotyping SNP data) and corresponding metadata. A discussion of the inheritance dataset and SNP data is provided in the present disclosure with reference to the genetic data store 205 of FIG. 2.

Using the inheritance dataset, the computing server 130 may perform various analyses of the target individual. For example, computing server 130 may apply a machine learning model to predict the traits (data manifestations) of the individual. The machine learning model may include any one of a logistic regression model, an extreme gradient boosting, or a gradient boosting machine. While the foregoing examples of machine learning models are described, it will be nevertheless appreciated that the disclosure is not limited thereto; rather, the machine learning model of embodiments may be implemented as any suitable machine learning modality, rule-based approach, or combination thereof as suitable. The machine learning model may be trained, for example by the computing server 130, with training data including the PRS of training individuals.

For example, the computing server 130 may input a feature vector including at least the PRS corresponding to the individual into the machine learning model. The PRS may be determined as discussed above or using any suitable means. The input feature vector may further include the age, sex, or ethnicity of the individual to improve the accuracy of trait predictions. While components of the feature, such as age, sex, or ethnicity, are mentioned, it will nevertheless be appreciated that the disclosure is not limited thereto; rather, the disclosure extends to and contemplates any other suitable factor or datum that may be utilized for attribution of trait inheritance. The machine learning model, which may be a classifier model, may output indicators of one or more traits associated with the individual. These outputs are received by the computing server 130 for further processing. The model utilized for performing trait prediction based on an input including, e.g., PRSs, may vary based on trait. For example, tree-based approaches such as XGBoost, may be utilized to perform binary classifications while logistic regression is used to perform non-binary classifications.

In some embodiments, the computing server 130 may use the phenotype calling engine 325 to predict the traits of the individual. In particular, the phenotype calling engine 325 can predict a specific trait of the individual by comparing the individual's PRS with a predetermined PRS threshold. Features of the phenotype calling engine 325 are discussed in the present disclosure in reference to FIG. 3.

In some embodiments, the computing server 130 may use the machine learning model 330 to predict the traits of the individual. Features of the machine learning model 330 are discussed in the present disclosure in reference to FIG. 3.

Responsive to receiving and/or predicting one or more traits of the individual, the computing server 130 can determine one of the first and second parents as having a measure of influence on one or more of the traits associated with the individual. The computing server 130 can select a threshold as a metric for discerning the measure of influence of each one of the first and second parents. The threshold is selected to segment instances where one parent has a dominant influence from those instances where both parents have an equal influence. This segmentation may provide a more nuanced understanding of trait influence from parents. The computing server 130 can process and analyze the individual's inheritance dataset including SNP data to predict parental influences on one or more traits of the individual. The analysis of the parental influences is described in step 520 through step 560.

Continuing with reference to FIG. 5, in some embodiments, the computing server 130 can determine a first portion and a second portion of the inheritance dataset of the individual, the first portion associated with a first parent, and the second portion associated with a second parent (step 520).

For example, the computing server 130 may sort the inheritance dataset of the individual into two parts, e.g. two haplotypes, each associated with one of two parents. This sorting may be accomplished through the process of genetic phasing, which assigns the pair of alleles received at each genetic locus to the individual's first parent or second parent.

In some embodiments, the computing server 130 may use the phasing engine 220 to generate the first and second portions of the inheritance dataset. Features of the phasing engine 220 are discussed in the present disclosure in reference to FIG. 2.

Continuing with reference to FIG. 5, in some embodiments, the computing server 130 can identify a subset of the data-bit regions that are associated with the data manifestation (step 530). For example, the computing server 130 may determine which SNP loci are statistically associated with a phenotypic trait. This determination process may be based on GWAS, and/or other processes that are described in reference to FIG. 3.

The computing server 130 may also determine a PRS for the individual based on the inheritance dataset at an identified subset of the SNP loci. The computing server 130 may calculate a weight for each SNP locus of the identified subset of SNP loci based on a p-value score for the SNP locus. The computing server 130 can calculate the PRS by summing over each product of a genotype of the individual at a SNP locus in the identified subset of SNP loci and a corresponding weight for the SNP locus. The computing server 130 may use the PRS calculation engine 315 to calculate the PRS for the individual for the identified subset of SNP loci. A discussion of the PRS determination by the PRS calculation engine 315 is provided in the present disclosure with reference to FIG. 3.

While an identified subset of SNP loci is described in embodiments, it will nevertheless be appreciated that the disclosure is not limited thereto; rather, in embodiments, alternative PRS approaches may be utilized as suitable. For example, an entirety or substantial entirety of available SNPs for one or more users may be utilized without a p-value threshold. In such applications, the SNPs are adjusted to a weighted value, which for some may go to zero. Such an approach may include the use of PRS-CSx.

Continuing with reference to FIG. 5, in some embodiments, the computing server 130 can determine a first source-specific association score representing a first measurement of association between the first data source and the data manifestation (step 540). The first source-specific association score may take the form a PRS associated with the first parent based on the first portion (e.g., a haplotype of the target individual inherited from the first parent) of the inheritance dataset at the identified subset of the SNP loci. The computing server 130 may use the PRS calculation engine 315 to calculate the PRS associated with the first parent based on the first portion of the inheritance dataset at the identified subset of the SNP loci.

Continuing with reference to FIG. 5, in some embodiments, the computing server 130 can determine a second source-specific association score representing a second measurement of association between the second data source and the data manifestation (step 550). The second source-specific association score may take the form a PRS associated with the second parent based on the second portion (e.g., a haplotype of the target individual inherited from the second parent) of the inheritance dataset at the identified subset of the SNP loci. The computing server 130 may use the PRS calculation engine 315 to calculate the PRS associated with the second parent based on the second portion of the inheritance dataset at the identified subset of the SNP loci.

Continuing with reference to FIG. 5, in some embodiments, the computing server 130 can identify at least one of the first data source and the second data source as having a measure of influence on the data manifestation of the named entity (step 560). This selection may be based on comparing the first source-specific association score to the second source-specific association score.

Thus, in situations where a user's PRS indicates that they are unlikely to be genetically predisposed to exhibiting a particular trait and their parents have highly disparate scores (one parent's haplotype suggesting high predisposition and one parent's haplotype suggesting low predisposition), the parent whose haplotype suggests low predisposition may be labeled as the more-influential parent for that trait. By contrast, in situations where a user's PRS indicates that they are likely to be genetically predisposed to exhibiting a particular trait and their parents have highly disparate scores (one parent's haplotype suggesting high predisposition and one parent's haplotype suggesting low predisposition), the parent whose haplotype suggests high predisposition may be labeled as the more-influential parent for that trait.

The computing server 130 may compare the PRS associated with the first and second parents. In some embodiments, responsive to a difference between the PRS associated with the first and second parents being greater than a predetermined threshold, the computing server 130 may select the parent with the higher PRS as having a dominant influence on the corresponding trait of the individual. In other embodiments, when the individual has a low PRS for a specific trait, the parent with the lower PRS may be selected as having the dominant influence on that specific trait. Responsive to the difference between the PRS between the first and second parents falling within the threshold, the computing server 130 may select both parents as having equal influence on the data manifestation of the named entity.

The computing server 130 may determine or select the threshold by determining, based on the comparison of the PRS of a plurality of first and second parents, a first decile dataset and a second decile dataset. The first decile dataset may represent a first decile of score similarity. In other words, the first decile dataset may represent the top 10% of the distribution of PRS similarity scores between the first and second parents of the plurality of first and second parents. For example, this means the pairs of parents in the first decile have the most similar PRSs. The second decile dataset may represent a second decile of score similarity. In other words, the second decile dataset may represent the bottom 10% of the distribution. The pairs of parents in the second decile may have the most different or dissimilar PRSs of the plurality of pairs of parents.

Figure 6A:
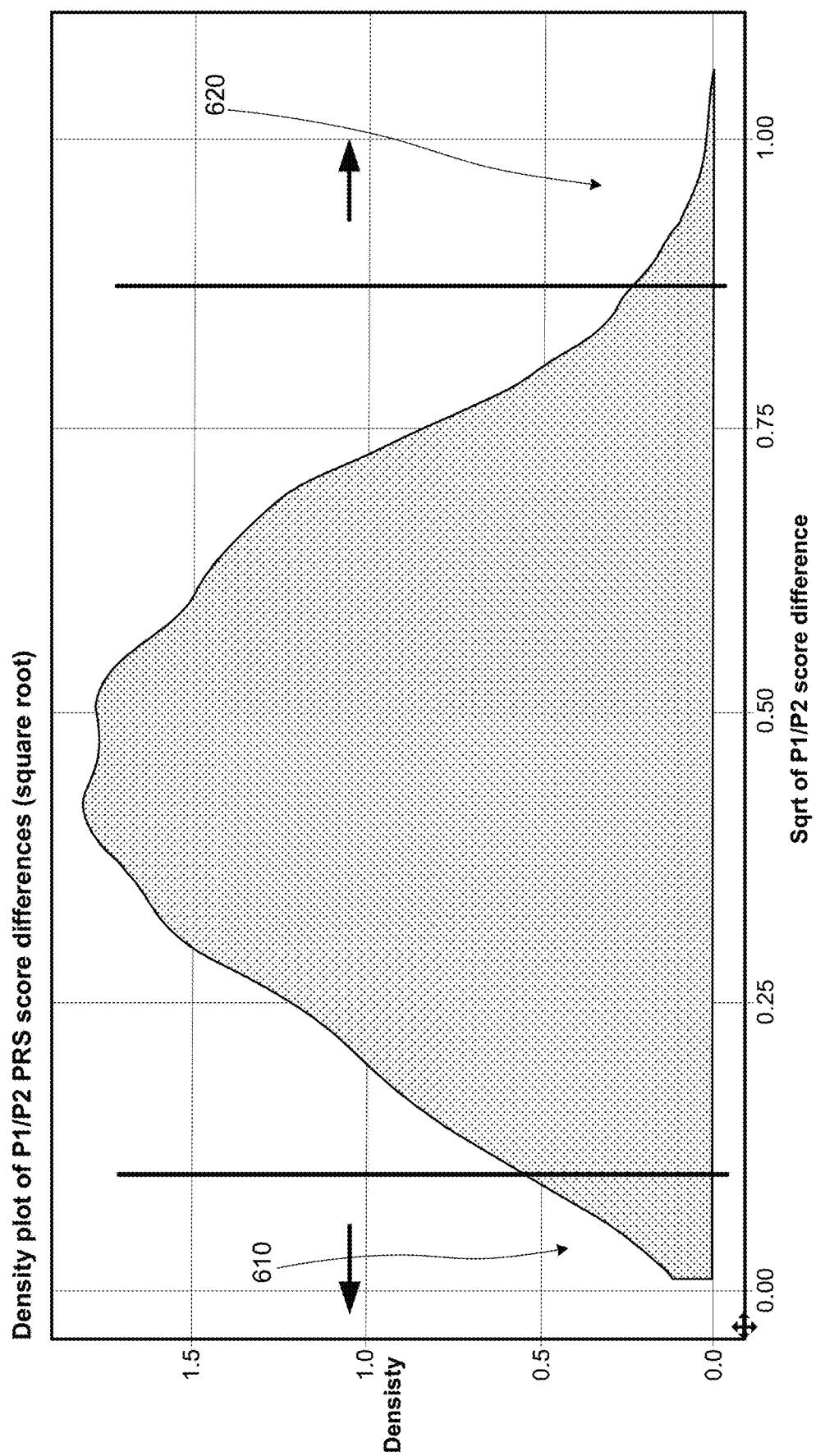
FIG. 6A illustrates a density plot of the PRS differences between the first and second parents, in accordance with some embodiments.

In some embodiments, trio data may refer to the inheritance data collected from a three-person family unit, typically consisting of two parents and one offspring. This data may provide a view of genetic transmission from both mother and father to the child. Using trio data, the computing server 130 may obtain the PRSs associated with the first and second parents (P1/P2 Diploid PRSs). The computing server may calculate a delta as the square root of the difference between the PRSs associated with the first and second parents. FIG. 6A shows the delta as a density plot 600. The density plot 600 represents the square root of the PRS differences between the first and second parents. FIG. 6A shows the first decile dataset 610 and a second decile dataset 620. The first decile dataset 610 may represent the top 10% of the distribution of PRS similarity scores between the first and second parents. The second decile dataset 620 may represent the bottom 10% of the distribution.

Discerning a meaningful and workable threshold between P1 and P2 is a challenge given the absence of ground-truth data on the differences between parental influences, but it has been surprisingly found that the use of trios advantageously allows for the generation and use of ground truth data for disambiguating P1, P2 score similarity. By obtaining P1 and P2 diploid PRSs (i.e. diploid PRSs for both parents in the trio for one or more traits) and determining a distribution of square roots of deltas therebetween, and, relying on top and bottom deciles of the distribution of deltas (i.e. relying on the most-different and most-similar parents for particular traits), and then obtaining deltas of customer parental P1/P2 scores (determined, e.g., using phased haplotypes) and choosing a threshold at a standard deviation below the mean of the distribution of users with the most-similar parents, anyone below the threshold is unusually similar in P1/P2 scores even in a cohort where parents already have similar diploid PRSs. In such a situation, a "both parents are influential" prediction becomes meaningful to a user.

While some embodiments rely upon a top 10% and bottom 10% of the distribution of the square root of differences between PRSs, it will be appreciated that the disclosure is not limited thereto. Rather, the analysis may utilize any suitable discretization, manipulation, or application of PRS or other data to discern a measure of influence of one data source on another data source, e.g. of a parent's haplotype on a target individual's likelihood of having a phenotypic trait. As such, any suitable strata and associated thresholds may be utilized, and may differ by trait and/or by population. For example, particular identified ethnic or community groups may have different traits distributions or features than other ethnic or community groups, such that a different threshold(s) is applied to the different groups for that particular trait.

The computing server 130 may determine trait scores for each parent based on the first decile dataset 610 and the second decile dataset 620. For example, the computing server 130 can compute trait scores for each parent in both the first decile dataset 610 (parents with very similar PRSs) and the second decile dataset 620 (parents with very different PRSs). The distribution of these scores yields two new datasets: a third dataset and a fourth dataset.

Figure 6B:
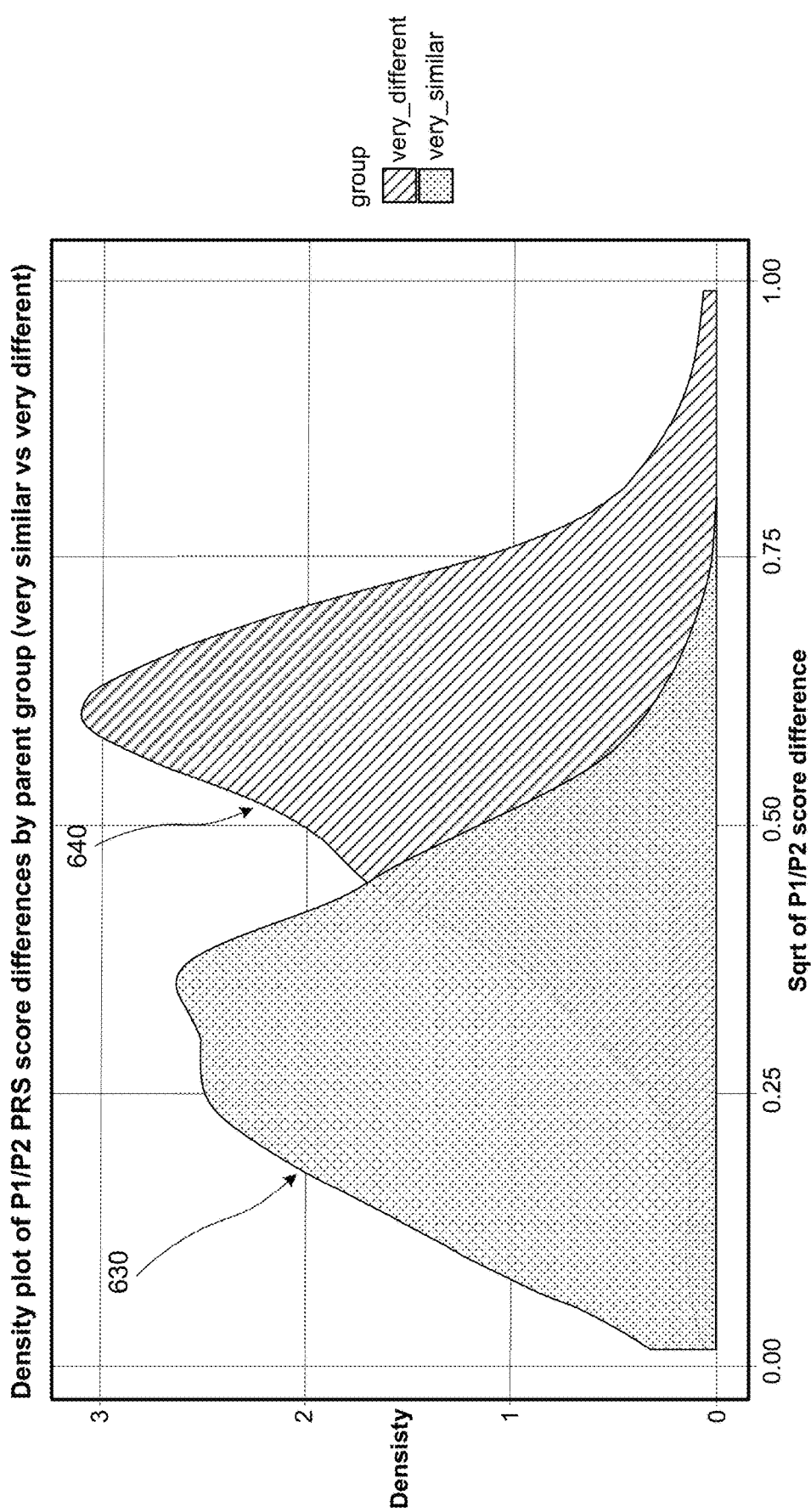
FIG. 6B illustrates datasets represents trait scores from parent pairs with substantially similar and different PRS, in accordance with some embodiments.
Figure 6C:
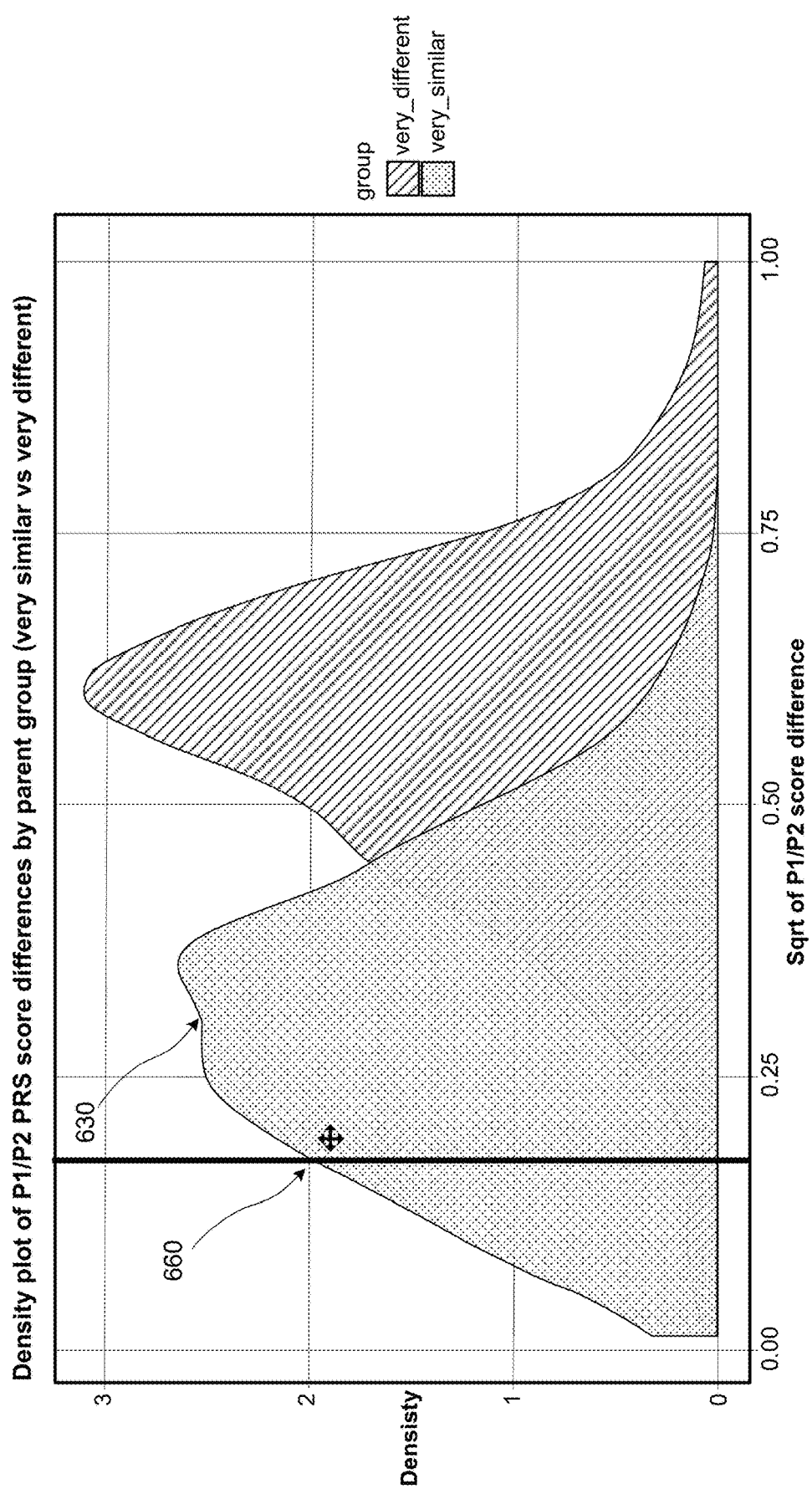
FIG. 6C illustrates selection of a threshold as one standard deviation below the mean of a third dataset, in accordance with some embodiments.

The third dataset represents trait scores from the parent pairs with substantially similar PRSs, including parents whose PRS are within the highest similarity group (from the first decile dataset 610). The fourth dataset represents the trait scores from the parent pairs with substantially different PRSs, including parents whose PRSs are within the lowest similarity group (from the second decile dataset 620). For example, FIG. 6B shows the third dataset 630 and the fourth dataset 640.

The computing server 130 may set the PRS threshold based on the third dataset, or a combination of the third dataset and fourth dataset. In some embodiments, the computing server 130 may determine a mean of the third dataset and set the threshold as one standard deviation below the determined mean. The threshold may provide a cut-off point. In some embodiments, if a difference observed between the PRSs of the two parents is above this threshold, one parent is determined to have a dominant influence. In some embodiments, if the PRS difference is less than or equal to the threshold, then both parents may be considered to equally influence the trait. For example, in FIG. 6C, the threshold 660 is selected as one standard deviation below the mean of the third dataset 630.

Further detail and examples in determining parental influence are described in the section below.

Example Embodiment of Determining Parental Influence on Genetically Influenced Traits The embodiments of the present disclosure facilitate splitting an individual's traits between a first parent and a second parent, "P1" and "P2," according to one or both parents' influence on the trait. Both parents may be equally influential, or one parent may be more influential than the other. The availability of phased data that can be attributed to parents facilitates the attribution of influence to the respective parents.

Traits can be complex and influenced by many genetic markers, each of which may have a small effect. For example, in one trait, a genetic marker RS123 (G/A) may have an effect allele A, with an odds ratio of 0.993567, which means that that allele's presence means that the individual is slightly less likely to exhibit the trait, whereas a different genetic marker RS456 (T/C), with effect allele T, may have an odds ratio of 1.01308, meaning that the presence of T makes the individual slightly more likely to exhibit the trait.

These odds ratios may be summed in a PRS representing the weighted sum of statistically significant alleles for a particular trait weighted by their effect sizes. PRSs may be used to fit a model and predict a trait probability for an individual. While odds ratios (which are frequently utilized in conjunction with logistic regression) have been described, it will nevertheless be appreciated that the disclosure is not limited thereto, but rather the disclosure contemplates the use of any effect-size estimate or model parameter as weights. For example, GWAS could be conducted using linear regression, mixed models, or otherwise as suitable, with suitable corresponding parameters or features allowing for trait prediction and attribution of a measure of influence to one or both parents.

Indeed, PRS may be generated for each trait by using phased data. This allows for calculating the PRS for the individual, and then for the haploid or haplotype that is attributable to P1 and for the haploid or haplotype that is attributable to P2.

An individual's PRS for a particular trait may be compared against the PRSs for each haplotype. Thus, for a particular trait, such as being a "morning person," an individual may have a high PRS, with a P1 PRS being 0.03 and a P2 PRS being −0.05, which in general would indicate that the user was more influenced in being genetically predisposed for exhibiting this trait by P1. Conversely, if the user's PRS was low/negative, it would be determined that P2 was more influential in the user not being genetically predisposed for exhibiting this trait.

For example, as shown in Table 3 below, the measure of influence of parents, e.g. parent-specific PRSs, may be determined based on effect alleles' presence in the phased haplotypes attributable to the parents, and in view of the associated weights.

In order to more accurately and meaningfully parse close calls between P1 and P2, an implementation for determining thresholds between P1 and P2 has been developed and is utilized in embodiments.

Figure 7:
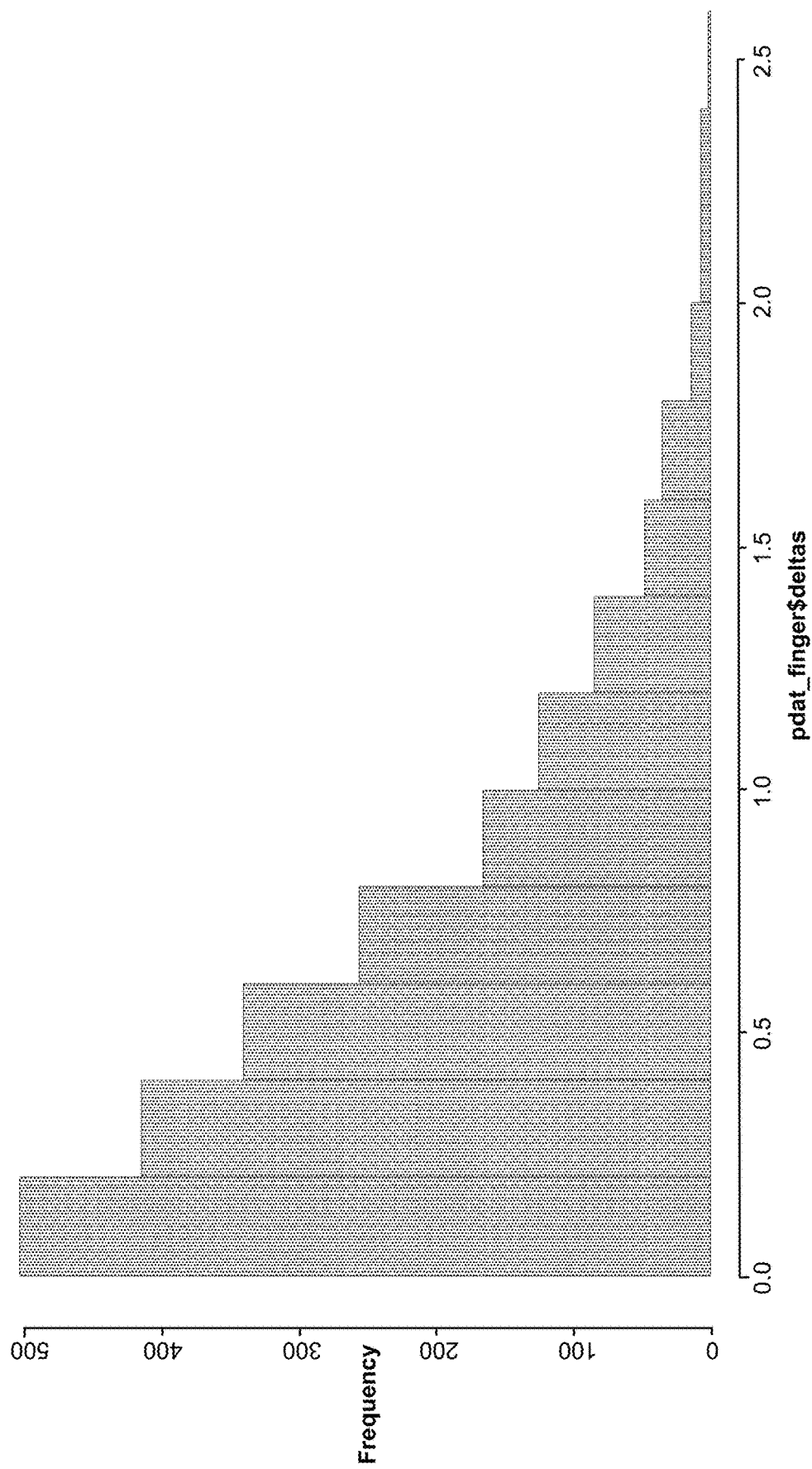
FIG. 7 illustrates a distribution of deltas in a group of samples, in accordance with some embodiments.

It has been found that a threshold for a delta between the P1 and P2 PRSs for a particular trait may be determined by taking a distribution of the deltas in a group of samples as seen in FIG. 7.

Figure 8:
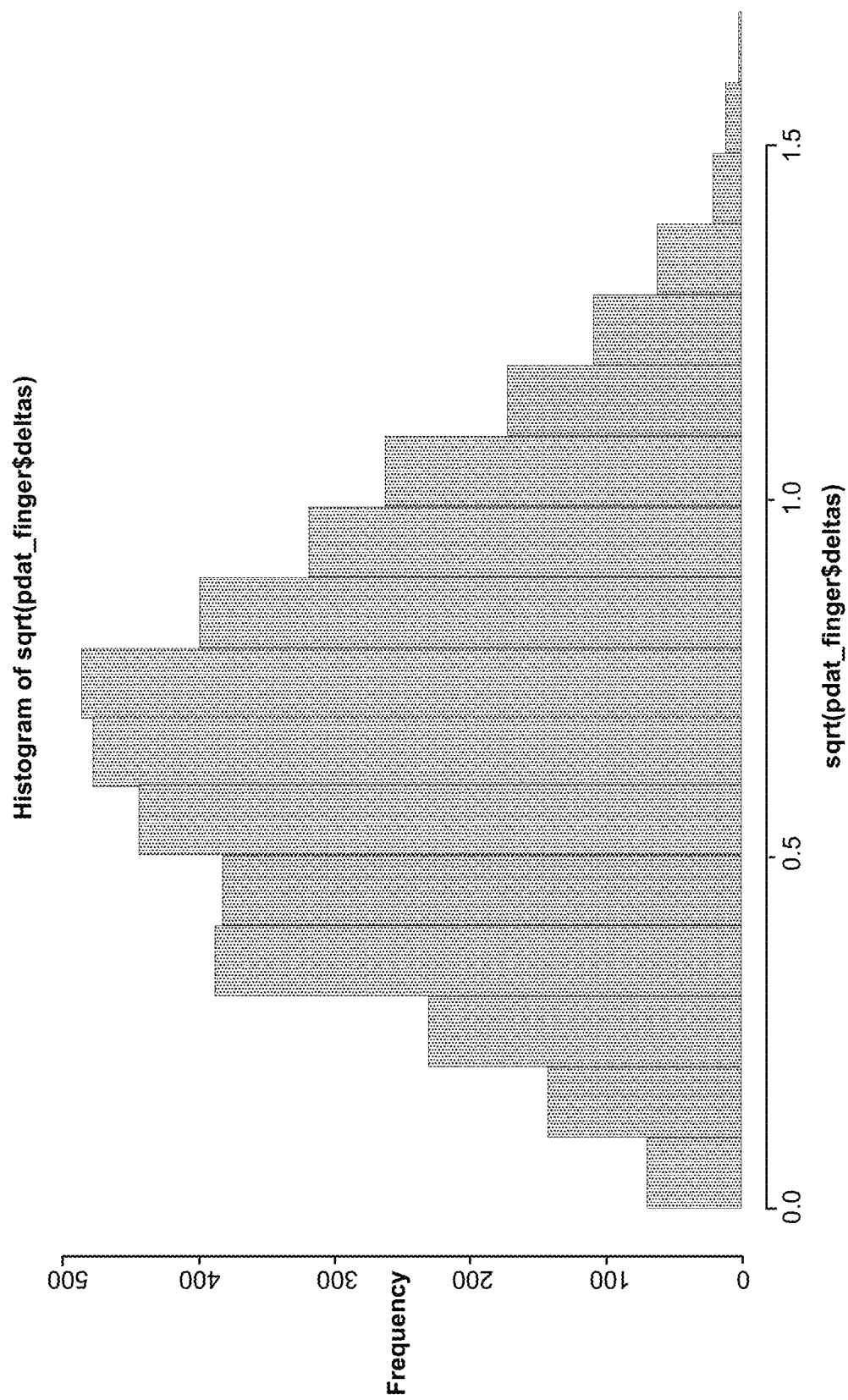
FIG. 8 illustrates a normal distribution of deltas of FIG. 7.

Taking the square roots of the deltas in the samples shown in FIG. 7 yields the normal distribution shown in FIG. 8. The distribution in FIG. 8 has been observed to be consistent across a plurality of traits, but it was determined to be unsatisfactorily arbitrary to set a simple standard deviation-based cutoff based on this distribution. An approach includes the use of trio data (two parents plus offspring genetic data and associated metadata). The approach includes taking a trait PRS and calculating parents' actual PRSs using trios including the full genomes for the parents. In an embodiment, some 300,000 trios may be used.

Figure 9:
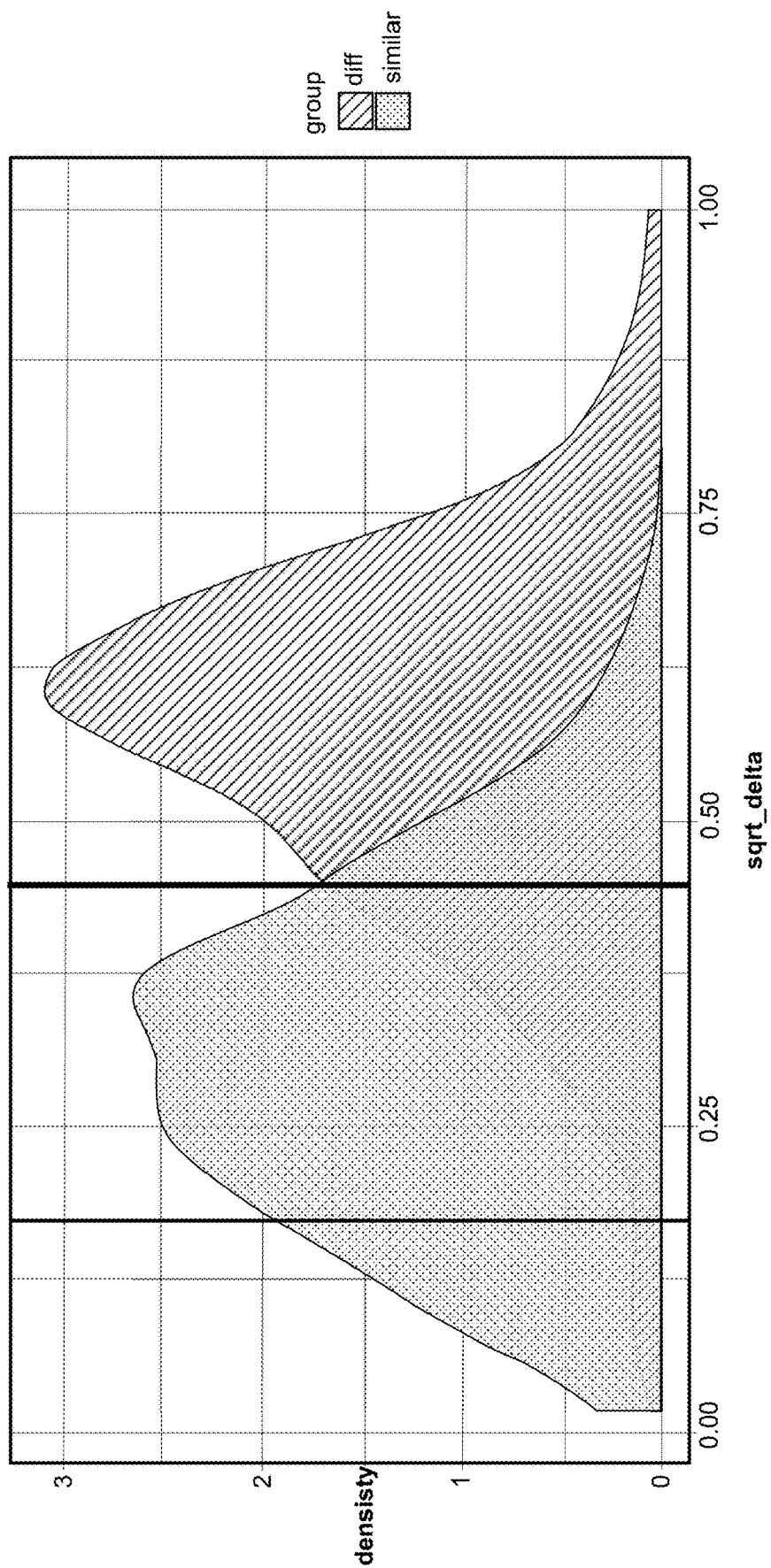
FIG. 9 illustrates the samples of FIG. 8 split into two groups.

In an embodiment, the samples may be split into two groups as shown in FIG. 9: those samples for which parents' diploid trait PRSs are most similar, and those samples for which parents' diploid trait PRSs are most different. The distribution of deltas in these two groups have been surprisingly found to have different normal distributions. In an embodiment, the intersection between these groups may be chosen as a cutoff, but this may result in greater than 50% of users having a result of "BOTH" parents influenced a trait.

Another embodiment is to use a cutoff based on the population of most-similar samples. Taking a cutoff of one standard deviation below the mean of this distribution may result in a better result which tells individuals when their parents are unusually similar, yielding a result of "BOTH." This balances the emotional engagement of a user with the nuances of similarity between parents. In one trait, this means that 14% of users will receive a "BOTH" label, though the number is different in different traits.

This process may be repeated across each trait that is reported to users by a genealogical and/or genetic research service. While a single standard deviation below the mean for the most-similar group has been described, it will be appreciated that the disclosure is not limited thereto, but

TABLE 3

| SNP | Effect Allele | Score | P1 Allele | P1 Weights | P2 Alleles | P2 Scores |
|---|---|---|---|---|---|---|
| SNP1 (A/G) | A | −0.01 | G | — | A | −0.01 |
| SNP2 (C/T) | T | 0.05 | T | 0.05 | T | 0.05 |
| SNP3 (A/C) | A | 0.06 | C | — | C | — |
| SNP4 (G/T) | T | 0.12 | G | — | T | 0.12 |
| SNP5 (A/C) | A | −0.03 | C | — | A | −0.03 |
| Total | | | | 0.05 | | 0.13 |

A challenge arises in situations where PRSs for P1 and P2 are similar, including but not limited to situations where the parental PRSs are similar to the individual PRS. It has been surprisingly found that users do not engage emotionally with an abundance of traits predictions that indicate that "both" parents were influential, which might be interpreted as "equally influential." Rather, users engage emotionally with a finding that one parent was more influential than the other on a trait, particularly where this finding squares with the user's anecdotal observations.

rather the disclosure covers modifications, different approaches, and other thresholds.

Further, it will be appreciated that for some individuals, genotyping data and phasing approaches may not provide P1/P2 assignments consistently across the entirety of the genome or genotype, as such may be dependent on the availability of match data. In order to reduce potential confusion of users to whom this applies, the approaches described in embodiments may be limited to users for whom 75% or above of the trait-related SNPs are consistently phased, though this threshold is merely exemplary and any suitable threshold may be relied upon.

While parental traits have been described, it will be appreciated that in embodiments where a user's parent's genotype data is available, the same may be phased and the approach described herein applied to ascertain grandparental trait influence, great-grandparental trait influence, and so on.

Computing Machine Architecture

Figure 10:
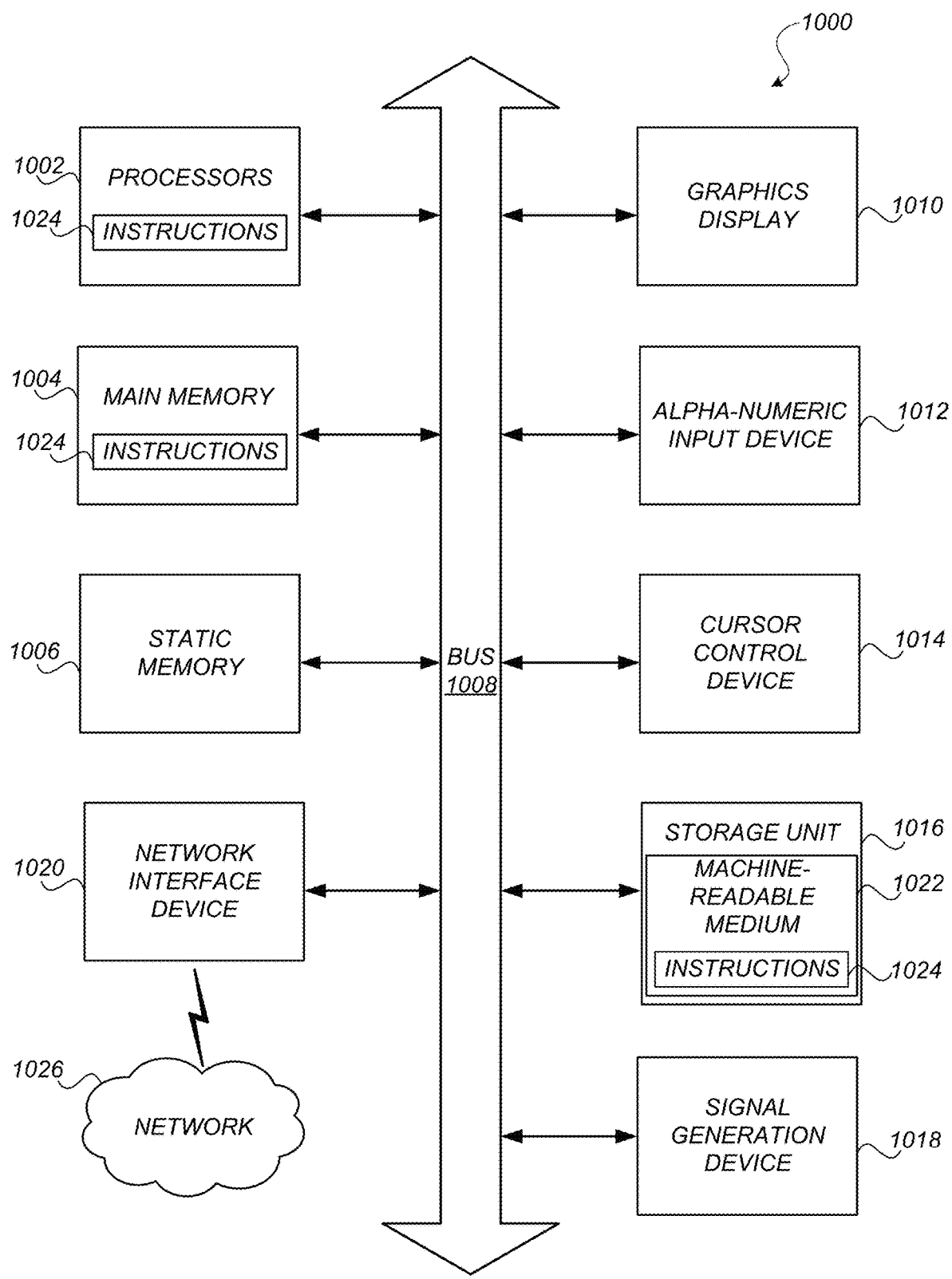
FIG. 10 is a block diagram of an example computing device, in accordance with some embodiments.

FIG. 10 is a block diagram illustrating components of an example computing machine that is capable of reading instructions from a computer-readable medium and executing them in a processor (or controller). A computer described herein may include a single computing machine shown in FIG. 10, a virtual machine, a distributed computing system that includes multiple nodes of computing machines shown in FIG. 10, or any other suitable arrangement of computing devices.

By way of example, FIG. 10 shows a diagrammatic representation of a computing machine in the example form of a computer system 1000 within which instructions 1024 (e.g., software, source code, program code, expanded code, object code, assembly code, or machine code), which may be stored in a computer-readable medium for causing the machine to perform any one or more of the processes discussed herein may be executed. In some embodiments, the computing machine operates as a standalone device or may be connected (e.g., networked) to other machines. In a networked deployment, the machine may operate in the capacity of a server machine or a client machine in a server-client network environment, or as a peer machine in a peer-to-peer (or distributed) network environment.

The structure of a computing machine described in FIG. 10 may correspond to any software, hardware, or combined components shown in FIGS. 1 and 2, including but not limited to, the client device 110, the computing server 130, and various engines, interfaces, terminals, and machines shown in FIG. 2. While FIG. 10 shows various hardware and software elements, each of the components described in FIGS. 1 and 2 may include additional or fewer elements.

By way of example, a computing machine may be a personal computer (PC), a tablet PC, a set-top box (STB), a personal digital assistant (PDA), a cellular telephone, a smartphone, a web appliance, a network router, an internet of things (IoT) device, a switch or bridge, or any machine capable of executing instructions 1024 that specify actions to be taken by that machine. Further, while only a single machine is illustrated, the terms "machine" and "computer" may also be taken to include any collection of machines that individually or jointly execute instructions 1024 to perform any one or more of the methodologies discussed herein.

The example computer system 1000 includes one or more processors 1002 such as a CPU (central processing unit), a GPU (graphics processing unit), a TPU (tensor processing unit), a DSP (digital signal processor), a system on a chip (SOC), a controller, a state equipment, an application-specific integrated circuit (ASIC), a field-programmable gate array (FPGA), or any combination of these. Parts of the computing system 1000 may also include a memory 1004 that stores computer code including instructions 1024 that may cause the processors 1002 to perform certain actions when the instructions are executed, directly or indirectly by the processors 1002. Instructions can be any directions, commands, or orders that may be stored in different forms, such as equipment-readable instructions, programming instructions including source code, and other communication signals and orders. Instructions may be used in a general sense and are not limited to machine-readable codes. One or more steps in various processes described may be performed by passing through instructions to one or more multiply-accumulate (MAC) units of the processors.

One or more methods described herein improve the operation speed of the processor 1002 and reduce the space required for the memory 1004. For example, the database processing techniques and machine learning methods described herein reduce the complexity of the computation of the processors 1002 by applying one or more novel techniques that simplify the steps in training, reaching convergence, and generating results of the processors 1002. The algorithms described herein also reduce the size of the models and datasets to reduce the storage space requirement for memory 1004.

The performance of certain operations may be distributed among more than one processor, not only residing within a single machine, but deployed across a number of machines. In some example embodiments, the one or more processors or processor-implemented modules may be located in a single geographic location (e.g., within a home environment, an office environment, or a server farm). In other example embodiments, one or more processors or processor-implemented modules may be distributed across a number of geographic locations. Even though the specification or the claims may refer to some processes to be performed by a processor, this may be construed to include a joint operation of multiple distributed processors. In some embodiments, a computer-readable medium comprises one or more computer-readable media that, individually, together, or distributedly, comprise instructions that, when executed by one or more processors, cause the one or more processors to perform, individually, together, or distributedly, the steps of the instructions stored on the one or more computer-readable media. Similarly, a processor comprises one or more processors or processing units that, individually, together, or distributedly, perform the steps of instructions stored on a computer-readable medium. In various embodiments, the discussion of one or more processors that carry out a process with multiple steps does not require any one of the processors to carry out all of the steps. For example, a processor A can carry out step A, a processor B can carry out step B using, for example, the result from the processor A, and a processor C can carry out step C, etc. The processors may work cooperatively in this type of situation such as in multiple processors of a system in a chip, in Cloud computing, or in distributed computing.

The computer system 1000 may include a main memory 1004, and a static memory 1006, which are configured to communicate with each other via a bus 1008. The computer system 1000 may further include a graphics display unit 1010 (e.g., a plasma display panel (PDP), a liquid crystal display (LCD), a projector, or a cathode ray tube (CRT)). The graphics display unit 1010, controlled by the processor 1002, displays a graphical user interface (GUI) to display one or more results and data generated by the processes described herein. The computer system 1000 may also include an alphanumeric input device 1012 (e.g., a keyboard), a cursor control device 1014 (e.g., a mouse, a trackball, a joystick, a motion sensor, or other pointing instruments), a storage unit 1016 (a hard drive, a solid-state drive, a hybrid drive, a memory disk, etc.), a signal generation device 1018 (e.g., a speaker), and a network interface device 1020, which also are configured to communicate via the bus 1008.

The storage unit 1016 includes a computer-readable medium 1022 on which is stored instructions 1024 embodying any one or more of the methodologies or functions described herein. The instructions 1024 may also reside, completely or at least partially, within the main memory 1004 or within the processor 1002 (e.g., within a processor's cache memory) during execution thereof by the computer system 1000, the main memory 1004 and the processor 1002 also constituting computer-readable media. The instructions 1024 may be transmitted or received over a network 1026 via the network interface device 1020.

While computer-readable medium 1022 is shown in an example embodiment to be a single medium, the term "computer-readable medium" should be taken to include a single medium or multiple media (e.g., a centralized or distributed database, or associated caches and servers) able to store instructions (e.g., instructions 1024). The computer-readable medium may include any medium that is capable of storing instructions (e.g., instructions 1024) for execution by the processors (e.g., processors 1002) and that cause the processors to perform any one or more of the methodologies disclosed herein. The computer-readable medium may include, but not be limited to, data repositories in the form of solid-state memories, optical media, and magnetic media. The computer-readable medium does not include a transitory medium such as a propagating signal or a carrier wave.

Additional Considerations

The foregoing description of the embodiments has been presented for the purpose of illustration; it is not intended to be exhaustive or to limit the patent rights to the precise forms disclosed. Persons skilled in the relevant art can appreciate that many modifications and variations are possible in light of the above disclosure.

Any feature mentioned in one claim category, e.g. method, can be claimed in another claim category, e.g. computer program product, system, or storage medium, as well. The dependencies or references in the attached claims are chosen for formal reasons only. However, any subject matter resulting from a deliberate reference back to any previous claims (in particular multiple dependencies) can be claimed as well, so that any combination of claims and the features thereof is disclosed and can be claimed regardless of the dependencies chosen in the attached claims. The subject matter may include not only the combinations of features as set out in the disclosed embodiments but also any other combination of features from different embodiments. Various features mentioned in the different embodiments can be combined with explicit mentioning of such combination or arrangement in an example embodiment or without any explicit mentioning. Furthermore, any of the embodiments and features described or depicted herein may be claimed in a separate claim and/or in any combination with any embodiment or feature described or depicted herein or with any of the features.

Some portions of this description describe the embodiments in terms of algorithms and symbolic representations of operations on information. These operations and algorithmic descriptions, while described functionally, computationally, or logically, are understood to be implemented by computer programs or equivalent electrical circuits, microcodes, or the like. Furthermore, it has also proven convenient at times, to refer to these arrangements of operations as engines, without loss of generality. The described operations and their associated engines may be embodied in software, firmware, hardware, or any combinations thereof.

Any of the steps, operations, or processes described herein may be performed or implemented with one or more hardware or software engines, alone or in combination with other devices. In some embodiments, a software engine is implemented with a computer program product comprising a computer-readable medium containing computer program code, which can be executed by a computer processor for performing any or all of the steps, operations, or processes described. The term "steps" does not mandate or imply a particular order. For example, while this disclosure may describe a process that includes multiple steps sequentially with arrows present in a flowchart, the steps in the process do not need to be performed in the specific order claimed or described in the disclosure. Some steps may be performed before others even though the other steps are claimed or described first in this disclosure. Likewise, any use of (i), (ii), (iii), etc., or (a), (b), (c), etc. in the specification or in the claims, unless specified, is used to better enumerate items or steps and also does not mandate a particular order.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein. In addition, the term "each" used in the specification and claims does not imply that every or all elements in a group need to fit the description associated with the term "each." For example, "each member is associated with element A" does not imply that all members are associated with an element A. Instead, the term "each" only implies that a member (of some of the members), in a singular form, is associated with an element A. In claims, the use of a singular form of a noun may imply at least one element even though a plural form is not used.

Finally, the language used in the specification has been principally selected for readability and instructional purposes, and it may not have been selected to delineate or circumscribe the patent rights. It is therefore intended that the scope of the patent rights be limited not by this detailed description, but rather by any claims that issue on an application based hereon. Accordingly, the disclosure of the embodiments is intended to be illustrative, but not limiting, of the scope of the patent rights.

The following applications are incorporated by reference in their entirety for all purposes: (1) U.S. Pat. No. 10,679,729, entitled "Haplotype Phasing Models," granted on Jun. 9, 2020, (2) U.S. Pat. No. 10,223,498, entitled "Discovering Population Structure from Patterns of Identity-By-Descent," granted on Mar. 5, 2019, (3) U.S. Pat. No. 10,720,229, entitled "Reducing Error in Predicted Genetic Relationships," granted on Jul. 21, 2020, (4) U.S. Pat. No. 10,558,930, entitled "Local Genetic Ethnicity Determination System," granted on Feb. 11, 2020, (5) U.S. Pat. No. 10,114,922, entitled "Identifying Ancestral Relationships Using a Continuous Stream of Input," granted on Oct. 30, 2018, (6) U.S. Pat. No. 11,429,615, entitled "Linking Individual Datasets to a Database," granted on Aug. 30, 2022, (7) U.S. Pat. No. 10,692,587, entitled "Global Ancestry Determination System," granted on Jun. 23, 2020, and (8) U.S. Patent Application Publication No. US 2021/0034647, entitled "Clustering of Matched Segments to Determine Linkage of Dataset in a Database," published on Feb. 4, 2021.

What is claimed is:

1. A computer-implemented method for predicting data-source influences on a data manifestation of a named entity, the computer-implemented method comprising:
   receiving an inheritance dataset of the named entity, the inheritance dataset comprising one or more reads at a plurality of data-bit regions;
   determining a first portion and a second portion of the inheritance dataset of the named entity, the first portion inherited from a first data source, and the second portion inherited from a second data source;
   identifying a subset of the data-bit regions that are associated with the data manifestation;
   determining a first source-specific association score representing a first measurement of association between the first data source and the data manifestation, wherein the first source-specific association score is determined based on the first portion of the inheritance dataset at the identified subset of the data-bit regions;
   determining a second source-specific association score representing a second measurement of association between the second data source and the data manifestation, wherein the second source-specific association score is determined based on the second portion of the inheritance dataset at the identified subset of the data-bit regions;
   comparing the first source-specific association score to the second source-specific association score; and
   identifying at least one of the first data source and the second data source as having a measure of influence on the data manifestation of the named entity.

2. The method of claim 1, wherein determining the first portion and the second portion of the inheritance dataset of the named entity comprises:
   using a phasing algorithm to generate the first portion and the second portion of the inheritance dataset.

3. The method of claim 1, wherein determining an association score based on the inheritance dataset at the identified subset of the data-bit regions comprises:
   calculating a weight for each data-bit region of the identified subset of the data-bit regions based on a p-value score for the data-bit region; and
   calculating an aggregated data-bit association score by summing over each product of data bit pattern at the data-bit region at the data-bit region and a corresponding weight for the data-bit region, wherein the aggregated data-bit association score is the association score.

4. The method of claim 1, wherein identifying at least one of the first data source and the second data source as having the measure of influence on the data manifestation of the named entity comprises:
   applying a machine learning model to predict the data manifestation of the named entity, wherein applying the machine learning model to predict the data manifestation of the named entity comprises inputting a feature vector comprising one or more association scores corresponding to the named entity into the machine learning model and receiving, from the machine learning model, an output indicating the data manifestation associated with the named entity; and
   responsive to receiving the data manifestation associated with the named entity, determining one of the first and second data sources as having the measure of influence on the data manifestation associated with the named entity.

5. The method of claim 4, wherein identifying at least one of the first data source and the second data source as having the measure of influence on the data manifestation of the named entity comprises:
   selecting a threshold as a metric for discerning the measure of influence of each one of the first and second data sources;
   comparing the source-specific association scores associated with the first and second data sources;
   responsive to a difference between the source-specific association scores associated with the first and second data sources greater than the threshold, selecting the data source with the higher association score as having a dominant influence on the data manifestation of the named entity; and
   responsive to the difference between the source-specific association scores between the first and second data sources falling within the threshold, selecting both data sources as having equal influence on the data manifestation of the named entity.

6. The method of claim 5, wherein selecting the threshold as the metric for discerning the measure of influence of each one of the first and second data sources comprises:
   determining, based on comparing the source-specific association scores of the first and second data sources, a first decile dataset and a second decile dataset, the first decile dataset representing a first decile of score similarity and the second decile dataset representing a second decile of score similarity;
   determining data manifestation scores for each data source based on the first and second decile datasets, wherein a distribution of the data manifestation scores provides a third dataset representing the data sources with substantially similar association scores and a fourth dataset representing the data sources with substantially different association scores; and
   setting the threshold based on the third dataset or a combination of the third and fourth datasets.

7. The method of claim 6, wherein setting the threshold based on the third dataset or a combination of the third and fourth datasets comprises:
   determining a mean of the third dataset; and
   setting the threshold as one standard deviation below the determined mean.

8. The method of claim 4, wherein the feature vector further comprises an age, sex, or ethnicity of the named entity to improve an accuracy of data manifestation predictions.

9. The method of claim 4, wherein the machine learning model comprises any one of:
   a logistic regression model;
   an extreme gradient boosting; or
   a gradient boosting machine.

10. The method of claim 4, further comprising
    training the machine learning model with training data comprising association scores of training named entities.

11. A system comprising:
    one or more processors; and
    memory configured to store instructions for predicting data-source influences on a data manifestation of a named entity, wherein the instructions, when executed by the one or more processors, cause the one or more processors to perform steps comprising:
      receiving an inheritance dataset of the named entity, the inheritance dataset comprising one or more reads at a plurality of data-bit regions;

determining a first portion and a second portion of the inheritance dataset of the named entity, the first portion inherited from a first data source, and the second portion inherited from a second data source;

identifying a subset of the data-bit regions that are associated with the data manifestation;

determining a first source-specific association score representing a first measurement of association between the first data source and the data manifestation, wherein the first source-specific association score is determined based on the first portion of the inheritance dataset at the identified subset of the data-bit regions;

determining a second source-specific association score representing a second measurement of association between the second data source and the data manifestation, wherein the second source-specific association score is determined based on the second portion of the inheritance dataset at the identified subset of the data-bit regions;

comparing the first source-specific association score to the second source-specific association score; and identifying at least one of the first data source and the second data source as having a measure of influence on the data manifestation of the named entity.

12. The system of claim 11, wherein determining the first portion and the second portion of the inheritance dataset of the named entity comprises:

using a phasing algorithm to generate the first portion and the second portion of the inheritance dataset.

13. The system of claim 11, wherein determining an association score based on the inheritance dataset at the identified subset of the data-bit regions comprises:

calculating a weight for each data-bit region of the identified subset of the data-bit regions based on a p-value score for the data-bit region; and calculating an aggregated data-bit association score by summing over each product of data bit pattern at the data-bit region at the data-bit region and a corresponding weight for the data-bit region, wherein the aggregated data-bit association score is the association score.

14. The system of claim 11, wherein identifying at least one of the first data source and the second data source as having the measure of influence on the data manifestation of the named entity comprises:

applying a machine learning model to predict the data manifestation of the named entity, wherein applying the machine learning model to predict the data manifestation of the named entity comprises inputting a feature vector comprising one or more association scores corresponding to the named entity into the machine learning model and receiving, from the machine learning model, an output indicating the data manifestation associated with the named entity; and responsive to receiving the data manifestation associated with the named entity, determining one of the first and second data sources as having the measure of influence on the data manifestation associated with the named entity.

15. The system of claim 14, wherein identifying at least one of the first data source and the second data source as having the measure of influence on the data manifestation of the named entity comprises:

selecting a threshold as a metric for discerning the measure of influence of each one of the first and second data sources;

comparing the source-specific association scores associated with the first and second data sources;

responsive to a difference between the source-specific association scores associated with the first and second data sources greater than the threshold, selecting the data source with the higher association score as having a dominant influence on the data manifestation of the named entity; and responsive to the difference between the source-specific association scores between the first and second data sources falling within the threshold, selecting both data sources as having equal influence on the data manifestation of the named entity.

16. The system of claim 15, wherein selecting the threshold as the metric for discerning the measure of influence of each one of the first and second data sources comprises:

determining, based on comparing the source-specific association scores of the first and second data sources, a first decile dataset and a second decile dataset, the first decile dataset representing a first decile of score similarity and the second decile dataset representing a second decile of score similarity;

determining data manifestation scores for each data source based on the first and second decile datasets, wherein a distribution of the data manifestation scores provides a third dataset representing the data sources with substantially similar association scores and a fourth dataset representing the data sources with substantially different association scores; and setting the threshold based on the third dataset or a combination of the third and fourth datasets.

17. The system of claim 16, wherein setting the threshold based on the third dataset or a combination of the third and fourth datasets comprises:

determining a mean of the third dataset; and setting the threshold as one standard deviation below the determined mean.

18. The system of claim 14, wherein the feature vector further comprises an age, sex, or ethnicity of the named entity to improve an accuracy of data manifestation predictions.

19. The system of claim 14, wherein the machine learning model comprises any one of:

a logistic regression model;

an extreme gradient boosting; or a gradient boosting machine.

20. A non-transitory computer readable medium for storing computer code comprising instructions, when executed by one or more computer processors, causing one or more computer processors to perform steps comprising:

receiving an inheritance dataset of the named entity, the inheritance dataset comprising one or more reads at a plurality of data-bit regions;

determining a first portion and a second portion of the inheritance dataset of the named entity, the first portion inherited from a first data source, and the second portion inherited from a second data source;

identifying a subset of the data-bit regions that are associated with the data manifestation;

determining a first source-specific association score representing a first measurement of association between the first data source and the data manifestation, wherein the first source-specific association score is determined based on the first portion of the inheritance dataset at the identified subset of the data-bit regions;

determining a second source-specific association score representing a second measurement of association between the second data source and the data manifestation, wherein the second source-specific association score is determined based on the second portion of the inheritance dataset at the identified subset of the data-bit regions;

comparing the first source-specific association score to the second source-specific association score; and identifying at least one of the first data source and the second data source as having a measure of influence on the data manifestation of the named entity.

* * * * *